(12) United States Patent
Stahl et al.

(10) Patent No.: US 11,730,977 B2
(45) Date of Patent: Aug. 22, 2023

(54) SYSTEMS AND METHODS FOR ADJUSTING MULTI-LEAF COLLIMATOR

(71) Applicant: SHANGHAI UNITED IMAGING HEALTHCARE CO., LTD., Shanghai (CN)

(72) Inventors: Johannes Stahl, Walnut Creek, CA (US); Walter Arturo Aguilar, Walnut Creek, CA (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 765 days.

(21) Appl. No.: 16/750,014

(22) Filed: Jan. 23, 2020

(65) Prior Publication Data

US 2021/0228908 A1 Jul. 29, 2021

(51) Int. Cl.
*A61N 5/10* (2006.01)
(52) U.S. Cl.
CPC ......... *A61N 5/1036* (2013.01); *A61N 5/1045* (2013.01); *A61N 2005/1074* (2013.01)
(58) Field of Classification Search
CPC .......... A61N 5/1036; A61N 2005/1074; A61N 5/1045
See application file for complete search history.

(56) References Cited

U.S. PATENT DOCUMENTS

| 6,052,430 A * | 4/2000 | Siochi ................. G21K 1/04 378/65 |
| 8,637,841 B2 | 1/2014 | Prince et al. |
| 2012/0043482 A1* | 2/2012 | Prince ................. G21K 1/046 250/505.1 |
| 2012/0105969 A1 | 5/2012 | Ehringfeld et al. |
| 2018/0193671 A1 | 7/2018 | Chappelow et al. |
| 2019/0175944 A1 | 6/2019 | Towe et al. |

FOREIGN PATENT DOCUMENTS

| CN | 102755696 A | 10/2012 |
| CN | 105288870 A | 2/2016 |

* cited by examiner

*Primary Examiner* — Christine H Matthews
*Assistant Examiner* — Joshua D Lannu
(74) *Attorney, Agent, or Firm* — Metis IP LLC

(57) ABSTRACT

The present disclosure provides systems and methods for adjusting a multi-leaf collimator (MLC) in a treatment process according to a treatment plan or a portion thereof. The MLC may include at least one closed leaf pair in the treatment process. The method may include: for each of the at least one closed leaf pair, determining an offset for the closed leaf pair; and causing the at least one closed leaf pair to move based on the determined at least one offset before or during the treatment process.

20 Claims, 11 Drawing Sheets

SYSTEMS AND METHODS FOR ADJUSTING MULTI-LEAF COLLIMATOR

TECHNICAL FIELD

The present disclosure generally relates to a multi-leaf collimator, and more particularly to systems and methods for adjusting a multi-leaf collimator.

BACKGROUND

Radiation therapy has been widely employed in cancer treatment in which ionizing radiation is guided towards a treatment region (e.g., a tumor) of an object. In radiation therapy, high-energy electromagnetic radiation beams and/or particles are delivered for killing or inhibiting the growth of undesired tissue. Generally, it is desirable to delimit the radiation rays so that the radiation dose is maximized in the treatment region and minimized in the healthy tissue of the object. A multi-leaf collimator (MLC) plays an important role in delimiting the radiation rays. An MLC can have a plurality of leaf pairs. Although care has been taken, the leakage of radiation between leaves can occur during beam delivery, which can induce an accumulation of undesired radiation in a particular place of healthy tissue of the object. Therefore, it is desirable to provide methods and systems for adjusting the MLC of a radiation delivery device, adjusting a leakage distribution of the MLC, and/or reducing an effect of radiation leakage through a leaf gap in radiation with MLC.

SUMMARY

In one aspect of the present disclosure, a method for adjusting a multi-leaf collimator (MLC) in a treatment process according to a treatment plan or a portion thereof is provided. The method may be implemented on at least one machine each of which has at least one processor and at least one storage device. The MLC may include at least one closed leaf pair in the treatment process. The method may include: for each of the at least one closed leaf pair, determining an offset for the closed leaf pair; and causing the at least one closed leaf pair to move based on the determined at least one offset before or during the treatment process.

In some embodiments, the determining an offset for the closed leaf pair may include: designating a random value as the offset.

In some embodiments, the method may further include: generating the random value for each of the at least one closed leaf pair by a random number generator.

In some embodiments, the treatment process may include one or more treatment fractions. The method may further include: generating the offset for each of the at least one closed leaf pair before or at a beginning of at least one treatment fraction of the one or more treatment fractions.

In some embodiments, the treatment process may include one or more treatment fractions. The method may further include: generating the offset for each of the at least one closed leaf pair before or at a beginning of a beam delivery in at least one treatment fraction of the one or more treatment fractions.

In some embodiments, the method may further include: determining the offset for each of the at least one closed leaf pair in a treatment planning process that generates the treatment plan before the treatment process.

In some embodiments, the offset of each of the at least one closed leaf pair may be no larger than a predetermined threshold. The predetermined threshold may be determined in a treatment planning process that generates the treatment plan before the treatment process.

In some embodiments, the method may further include: evaluating or adjusting the treatment plan based on a leakage distribution associated with a dose leakage of each of the at least one closed leaf pair.

In some embodiments, the treatment process may include one or more treatment fractions. The causing the at least one closed leaf pair to move based on the determined at least one offset may include: causing the at least one closed leaf pair to move, based on the determined at least one offset, dynamically within at least one treatment fraction of the one or more treatment fractions.

In some embodiments, the treatment process may include one or more treatment fractions. The causing the at least one closed leaf pair to move based on the determined at least one offset may include: causing the at least one closed leaf pair to move, based on the determined at least one offset, dynamically during a beam delivery in at least one treatment fraction of the one or more treatment fractions.

In some embodiments, the treatment process may include one or more treatment fractions. The causing the at least one closed leaf pair to move based on the determined at least one offset may include: causing a first closed leaf pair of the at least one closed leaf pair to move by a first offset in a first treatment fraction of the one or more treatment fractions; and/or causing the first closed leaf pair of the at least one closed leaf pair to move by a second offset in a second treatment fraction of the one or more treatment fractions.

In some embodiments, the treatment process may include one or more treatment fractions. The causing the at least one closed leaf pair to move based on the determined at least one offset may include: causing a third closed leaf pair of the at least one closed leaf pair to move by a third offset in a third treatment fraction of the one or more treatment fractions; and/or causing a fourth closed leaf pair of the at least one closed leaf pair to move by a fourth offset in the third treatment fraction of the one or more treatment fractions.

In some embodiments, the method may further include causing one or more open leaf pairs to move according to the treatment plan. The causing the at least one closed leaf pair to move based on the determined at least one offset may include: causing the at least one closed leaf pair to move based on the determined at least one offset when the one or more open leaf pairs are caused to move according to the treatment plan; or causing the at least one closed leaf pair to move based on the determined at least one offset when the one or more open leaf pairs are static.

In some embodiments, the method may further include determining the at least one closed leaf pair from one or more closed leaf pairs that are not covered by any jaw.

In some embodiments, the method may further include: determining a fifth leaf pair whose state is changed from open to closed during the treatment process; and/or after the fifth leaf pair is closed, causing the fifth leaf pair to move by a fifth offset.

In some embodiments, the method may further include: determining a sixth leaf pair whose status is changed from closed to open during the treatment process; during a period in which the sixth leaf pair is closed, causing the sixth leaf pair to move by a sixth offset; prior to opening the sixth leaf pair, causing the sixth leaf pair to move to a prescribed position according to the treatment plan; and/or causing the sixth leaf pair to move from the prescribed position according to the treatment plan.

In some embodiments, each of the at least one closed leaf pair may include a gap between the each closed leaf pair. The causing the at least one closed leaf pair to move based on the determined at least one offset may include: causing the at least one closed leaf pair to move based on the determined at least one offset so that a position of the gap between the each closed leaf pair is adjusted by a corresponding determined offset.

In some embodiments, the MLC may include at least two layers of leaves. The at least two layers of leaves may include a first layer and a second layer. The first layer may include a first closed leaf pair. The second layer may include a second closed leaf pair. The method may further include: generating a first random value and a second random value independently; causing the first closed leaf pair in the first layer to move based on the first random value; and/or causing the second closed leaf pair in the second layer to move based on the second random value.

In another aspect of the present disclosure, a system for adjusting a multi-leaf collimator (MLC) in a treatment process according to a treatment plan or a portion thereof is provided. The MLC may include at least one closed leaf pair in the treatment process. The system may include: a drive mechanism configured to drive the at least one closed leaf pair to move; and a controller configured to: for each of the at least one closed leaf pair, determining an offset for the closed leaf pair; and causing the at least one closed leaf pair to move based on the determined at least one offset before or during the treatment process.

In another aspect of the present disclosure, a system for adjusting a multi-leaf collimator (MLC) in a treatment process according to a treatment plan or a portion thereof is provided. The MLC may include at least one closed leaf pair in the treatment process. The system may include: at least one storage device storing a set of instructions; and at least one processor in communication with the storage device. When executing the set of instructions, the at least one processor may be configured to cause the system to perform operations including: for each of the at least one closed leaf pair, determining an offset for the closed leaf pair; and causing the at least one closed leaf pair to move based on the determined at least one offset before or during the treatment process.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order.

However, the terms may be displaced by another expression if they achieve the same purpose.

Figure 2:
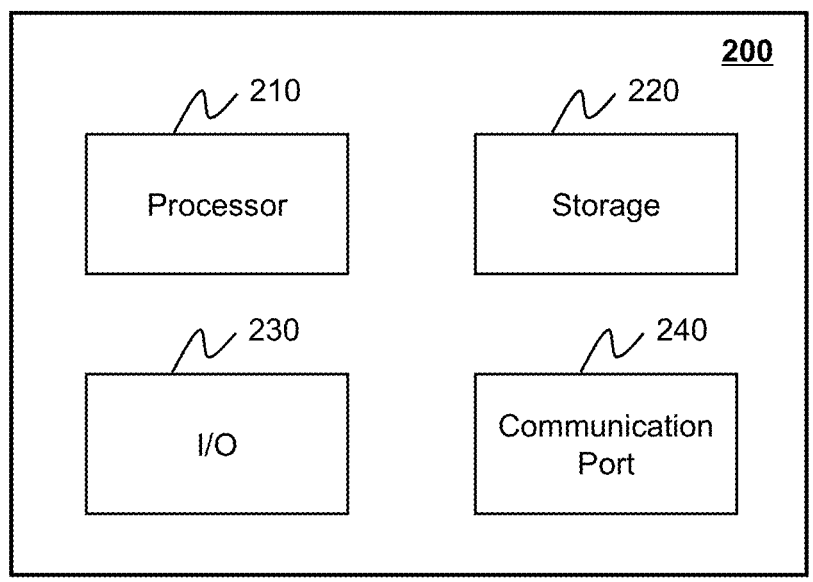
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

The present disclosure relates to systems and methods for adjusting a multi-leaf collimator (MLC) of a radiation delivery device, adjusting a leakage distribution of a multi-leaf collimator, and/or reducing an effect of leaf gap leakage in radiation with MLC. Because of the existence of a leaf gap between leaves (e.g., between leaves of a closed leaf pair of the MLC), radiation leakage through the leaf gap may occur. In the present disclosure, position(s) of one or more closed leaf pairs of the MLC may be adjusted in a treatment process, so that the leakage distribution of the leaf gap(s) of the MLC may be adjusted or changed, and the effect of the leaf gap leakage may be mitigated. Specifically, in some embodiments, one or more offsets may be determined for one or more closed leaf pairs before or at the beginning of a treatment fraction or a beam delivery, and the one or more closed leaf pairs may be driven to move by the corresponding offset(s) so that position(s) of leaf gap(s) between the closed leaf pair(s) may be adjusted. In some embodiments, the offsets may have random values, and the position(s) of the leaf gap(s) between the closed leaf pair(s) may be dispersed at random, and thus the leaf gap leakage between the closed leaf pair(s) may be dispersed at random. By adjusting the closed leaf pairs, an accumulation of leakage dose in a specific spot (i.e., hot spot(s)) may be avoided or mitigated. For example, the leaf gap leakage may be distributed, instead of being accumulated on a specific spot of a critical organ. Therefore, the effect of leaf gap leakage on normal tissues (e.g., a critical organ) can be reduced or mitigated without a complicated modification of or complex operations to a current radiation device (e.g., a radiotherapy device).

Figure 1:
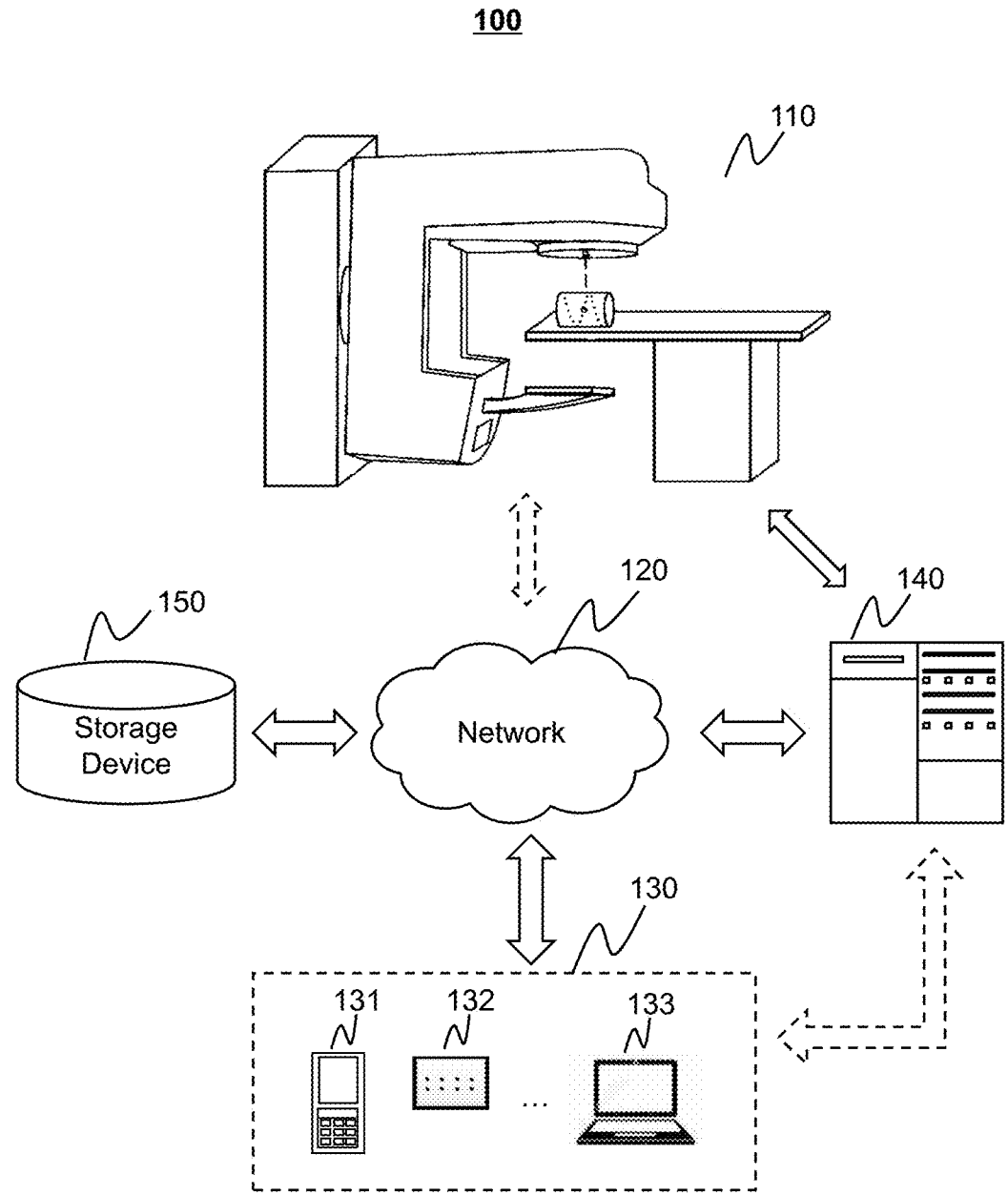
FIG. 1 is a schematic diagram illustrating an exemplary radiotherapy system according to some embodiments of the present disclosure.

FIG. 1 is a schematic diagram illustrating an exemplary radiotherapy system according to some embodiments of the present disclosure. As shown in FIG. 1, the radiotherapy system 100 may include a radiation delivery device 110, a network 120, one or more terminals 130, a processing device 140, and a storage device 150. In some embodiments, the terminal(s) 130 may be used as upper computer(s) (or host computer(s)), while the processing device 140 may be used as a lower computer (or a slave computer). The components in the radiotherapy system 100 may be connected in one or more of various ways. Merely by way of example, the radiation delivery device 110 may be connected to the processing device 140 directly (e.g., via optical fiber (e.g., a peripheral component interconnect express (PCI-E) cable)). As another example, the radiation delivery device 110 may be connected to the processing device 140 through the network 120 as indicated by the bi-directional arrow in dotted lines linking the radiation delivery device 110 and the network 120. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

In some embodiments, the radiation delivery device 110 may be a radiotherapy (RT) device. In some embodiments, the RT device may deliver one or more radiation beams to a treatment region (e.g., a tumor) of an object (e.g., a patient) for causing an alleviation of the object's symptom. In some embodiments, the RT device may be a conformal radiation therapy device, an image guided radiation therapy (IGRT) device, an intensity modulated radiation therapy (IMRT) device, an intensity modulated arc therapy (IMAT) device, or the like. In some embodiments, the RT device may include a linear accelerator (also referred to as "linac"). The linac may generate and emit a radiation beam (e.g., an X-ray beam) from a treatment head. The radiation beam may pass through one or more collimators (e.g., an MLC)) forming certain shapes, and enter into the object. In some embodiments, the radiation beam may include electrons, photons, or other types of radiation. In some embodiments, the energy of the radiation beam may be in the megavoltage range (e.g., >1 MeV), and may therefore be referred to as a megavoltage beam. The treatment head may be coupled to a gantry. The gantry may rotate, for example, clockwise or counter-clockwise around a gantry rotation axis. In some embodiments, the treatment head may rotate along with the gantry. In some embodiments, the RT device may further include a table configured to support the object during radiation treatment.

In some embodiments, the radiation delivery device 110 may further include one or more MLCs (not shown in FIG. 1). The MLC(s) may be configured to collimate radiation beam(s) of the radiation delivery device 110 and/or define the beam shape(s) thereof. In some embodiments, the MLC may include a plurality of leaves. The plurality of leaves may form an aperture. The aperture may define or modify the shape of the beam that is delivered to the object. In some embodiments, one or more leaves of the MLC may be moved according to a treatment plan. In some embodiments, the shape of the aperture may be changed according to a desired segment shape of the treatment plan. In some embodiments, the treatment plan may be generated by a treatment planning system (TPS) associated with the radiotherapy system 100.

In some embodiments, the radiation delivery device 110 may further include a drive mechanism (not shown in FIG. 1) configured to drive the leaves to move. In some embodiments, the drive mechanism may include one or more driving circuits (not shown in FIG. 1). In some embodiments, a driving circuit may generate driving signal(s) to drive the leaves of the MLC to move towards target position(s) during treatment. In some embodiments, the driving circuits may be set in the radiation delivery device 110, and may communicate with the processing device 140 via the connection between the radiation delivery device 110 and the processing device 140. For example, the processing device 140 may provide (or send) a control signal to the drive circuit, and accordingly, the drive circuit may generate a driving signal to cause, e.g., one or more actuators to drive the leaves to move towards the target position(s).

In some embodiments, the radiation delivery device 110 may further include one or more actuators configured to actuate the leaves to move. In some embodiments, an actuator may actuate the leaves to move according to a driving signal. In some embodiments, each leaf may be actuated by an actuator. Exemplary actuators may be associated with a hydraulic drive mechanism, a spring-based drive mechanism, an electric-charge-based drive mechanism, a magnetic drive mechanism, a pneumatic drive mechanism, or the like, or a combination thereof. In the following descriptions, motors are described for illustration purpose; it should be noted that any other type of actuators can be used to actuate the leaves to move when using the driving methods and systems of the present disclosure.

In some embodiments, the radiation delivery device 110 may further include one or more position detection devices (not shown in FIG. 1). A position detection device may be configured to detect a current position of a leaf, and/or a current velocity of the leaf directly or indirectly. In some embodiments, the position detection device may detect a displacement of the leaf, and the current position of the leaf may be determined based on the displacement of the leaf and an initial position of the leaf, and accordingly, the current velocity of the leaf may be determined based on the displacement of the leaf and a time for the leaf movement. Exemplary position detection device(s) may include a magnetic displacement sensor (e.g., a Hall effect sensor), a grating displacement sensor, an encoder (e.g., an encoder mounted on an actuator (e.g., a motor, a cylinder, or the like)), a potentiometer (e.g., a potentiometer mounted on a motor), or the like, or any combination thereof. In some embodiments, a leaf may have a corresponding position detection device.

In some embodiments, a leaf may have two corresponding position detection devices. For example, the leaf may have a magnetic displacement sensor and a potentiometer. The displacements of the leaf detected by the two position detection devices may be used to determine whether the leaf movement is abnormal.

In some embodiments, the current position of a leaf and/or the current velocity of the leaf may be transmitted to the processing device 140 (e.g., the control module 904) to generate control signal(s). In some embodiments, the processing device 140 may control a leaf to move based on the current position of the leaf and/or the current velocity of the leaf. In some embodiments, the current position of a leaf and/or the current velocity of the leaf may be further transmitted to the terminal(s) 130 for display.

In some embodiments, the object to be treated or scanned (also referred to as imaged) may include a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc.

The network 120 may include any suitable network that can facilitate exchange of information and/or data for the radiotherapy system 100. In some embodiments, one or more components of the radiotherapy system 100 (e.g., the radiation delivery device 110, the terminal(s) 130, the processing device 140, the storage device 150, etc.) may communicate information and/or data with one or more other components of the radiotherapy system 100 via the network 120. For example, the processing device 140 may obtain data corresponding to the leaves of the MLC from the radiation delivery device 110 via the network 120. As another example, the processing device 140 may obtain user instructions from the terminal(s) 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiotherapy system 100 may be connected to the network 120 to exchange data and/or information.

Figure 3:
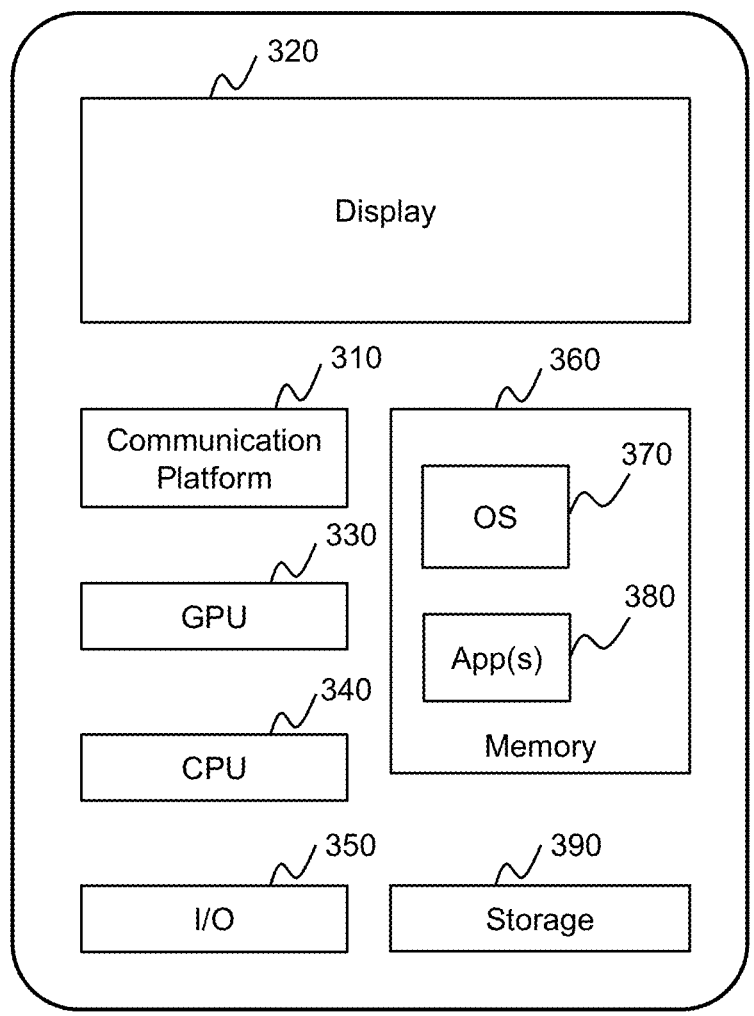
FIG. 3 is a schematic diagram illustrating exemplary hardware and/or software components of an exemplary mobile device on which the terminal may be implemented according to some embodiments of the present disclosure.

The terminal(s) 130 may enable interactions between a user and the radiotherapy system 100. The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140. In some embodiments, the terminal(s) 130 may remotely operate the radiation delivery device 110. In some embodiments, the terminal(s) 130 may operate the radiation delivery device 110 via a wireless connection. In some embodiments, the terminal(s) 130 may receive information and/or instructions inputted by a user, and send the received information and/or instructions to the radiation delivery device 110 or the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted. In some embodiments, the terminal(s) 130 may include a control handle, a control box, a console, etc. In some embodiments, a user may choose, through the terminal(s) 130 to enable or disable the performance of the leaves illustrated in FIG. 10.

The processing device 140 may process data and/or information obtained from the radiation delivery device 110, the terminal 130, and/or the storage device 150. For example, the processing device 140 may determine one or more closed leaf pairs of the multi-leaf collimator (MLC). As another example, the processing device 140 may determine one or more offsets for one or more closed leaf pairs. As still another example, the processing device 140 may cause one or more closed leaf pairs to move based on the corresponding determined offsets. As a further example, the processing device 140 may cause one or more open leaf pairs to move according to a treatment plan.

In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the radiation delivery device 110, the terminal 130, and/or the storage device 150 via the network 120. As another example, the processing device 140 may be directly connected to the radiation delivery device 110, the terminal 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

In some embodiments, components of the radiotherapy system 100 (e.g., the radiation delivery device 110, the terminal 130, the processing device 140) may communicate with each other in a treatment process. For example, before the treatment process starts, the terminal 130 may send instruction(s) or information related to prescribed position(s) of a leaf to the processing device 140. The processing device 140 may determine one or more closed leaf pairs of the multi-leaf collimator (MLC). As another example, before one or more treatment fractions starts, one or more offsets for at least one of the one or more closed leaf pairs may be determined by the processing device 140, and/or stored in the terminal 130. As a further example, during the treatment process, the radiation delivery device 110 may transmit the current positions of the closed leaf pairs to the processing device 140, and the processing device 140 may cause one or more closed leaf pairs to move based on the corresponding determined offsets, and/or the current positions of the closed leaf pairs. As still a further example, the processing device 140 may transmit the current positions of the closed leaf pairs to the terminal 130 for display.

The storage device 150 may store data, instructions, and/or any other information. In some embodiments, the storage device 150 may store data obtained from the radiation delivery device 110, the terminal 130 and/or the processing device 140. For example, the storage device 150 may store a treatment plan, parameters related to motion statuses of the leaves (e.g., a current position, an offset), or the like. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the radiotherapy system 100 (e.g., the processing device 140, the terminal 130, etc.). One or more components in the radiotherapy system 100 may access the data or instructions stored in the storage device 150 via the network 120. In some embodiments, the storage device 150 may be directly connected to or communicate with one or more other components in the radiotherapy system 100 (e.g., the processing device 140, the terminal 130, etc.). In some embodiments, the storage device 150 may be part of the processing device 140. In some embodiments, the processing device 140 may be connected to or communicate with the radiation delivery device 110 via the network 120, or at the backend of the processing device 140.

FIG. 2 is a schematic diagram illustrating exemplary hardware and/or software components of an exemplary computing device on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process data obtained from the radiation delivery device 110, the terminal 130, the storage device 150, and/or any other component of the radiotherapy system 100. In some embodiments, the processor 210 may determine one or more closed leaf pairs. In some embodiments, the processor 210 may determine one or more offsets for the one or more closed leaf pairs. In some embodiments, the processor 210 may cause the one or more closed leaf pairs to move based on the corresponding determined offsets. In some embodiments, the processor 210 may cause the one or more open leaf pairs to move according to a treatment plan. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the radiation delivery device 110, the terminal 130, the storage device 150, and/or any other component of the radiotherapy system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for driving the leaves of the MLC.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the radiation delivery device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiotherapy system 100 via the network 120. In some embodiments, a user may input parameters to the radiotherapy system 100, via the mobile device 300.

In order to implement various modules, units and their functions described above, a computer hardware platform may be used as hardware platforms of one or more elements (e.g., the processing device 140 and/or other components of the radiotherapy system 100 described in FIG. 1). Since these hardware elements, operating systems and program languages are common; it may be assumed that persons skilled in the art may be familiar with these techniques and they may be able to provide information needed in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

Figure 4:
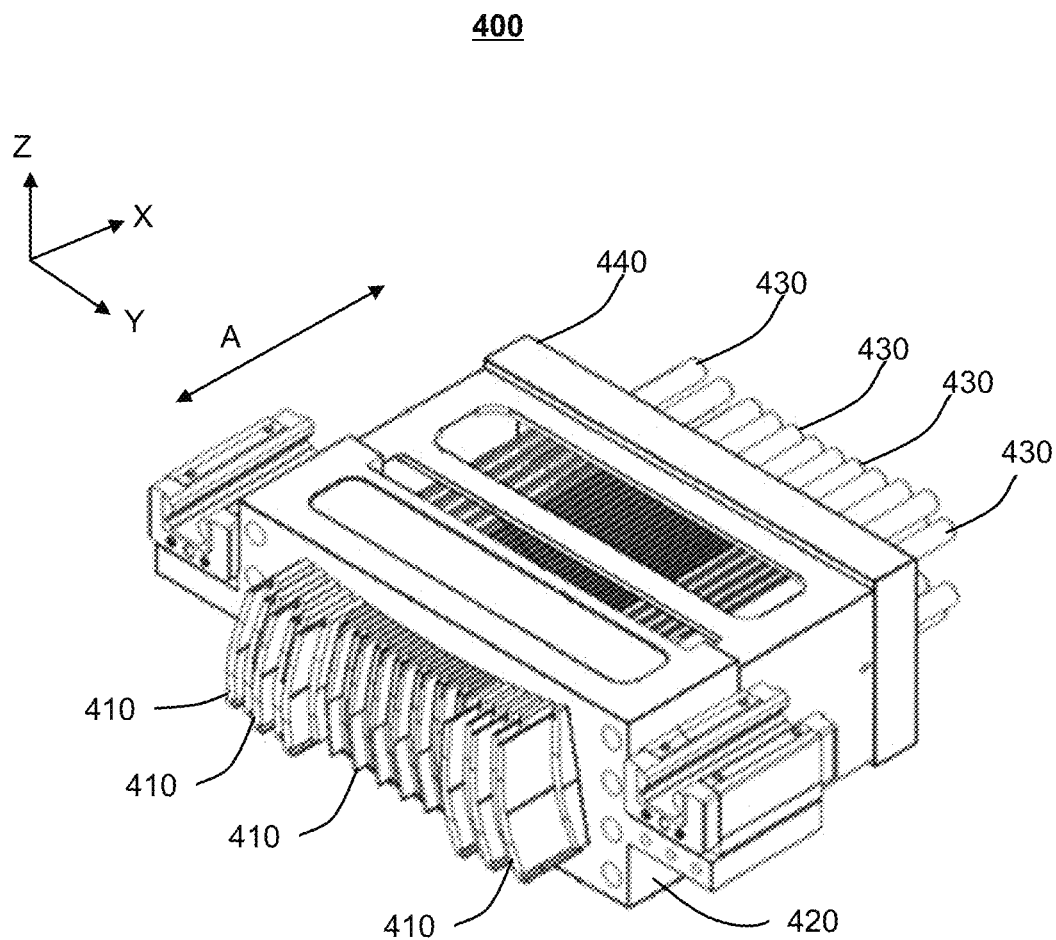
FIG. 4 is a schematic diagram illustrating a portion of an exemplary multi-leaf collimator (MLC) according to some embodiments of the present disclosure.

FIG. 4 is a schematic diagram illustrating a portion of an exemplary multi-leaf collimator (MLC) according to some embodiments of the present disclosure. Although only one bank of leaves are shown in FIG. 4 for illustration purposes, it should be noted that the MLC 400 may include two or more banks of leaves. For example, the MLC 400 may include two opposing banks arranged in a same level (i.e., a same plane). As another example, the MLC 400 may include two or more levels of leaves (i.e., two or more sets of leaves in two or more different planes, two or more layers of leaves, e.g., one on top of another), and each level (or layer) may include two opposing banks. As shown in FIG. 4, the MLC 400 may include a plurality of leaves 410, a rail box 440, one or more drive mechanisms 430, and a housing 420. In some embodiments, the housing 420 may be configured to accommodate the plurality of leaves 410, the drive mechanism(s) 430, etc. In some embodiments, the housing 420 may be connected with the rail box 440.

In some embodiments, the plurality of leaves 410 may be movable along a plurality of rails disposed on the rail box 440. In some embodiments, at least some leaves 410 of the plurality of leaves may be movable in a direction parallel to each another. In some embodiments, at least some of the leaves 410 may be configured to move simultaneously while the radiation delivery is off. The plurality of leaves 410 may be configured to shield a portion of radiation beams and form an aperture to allow a portion of the radiation beams to pass through. The portion of the radiation beams passing through the aperture may reach a treatment region of the object to perform the radiation therapy (RT). In some embodiments, the processing device 140 may control at least one leaf 410 of the MLC 400 to move into one or more positions to modify the shape of the aperture according to one or more parameters associated with the MLC 400 (e.g., a segment shape defined by the shape of the aperture formed by the MLC 400). The parameter(s) may be pre-determined by the processing device 140, or may be determined according to a specific condition as the specific condition occurs. Exemplary conditions may include that a scanned image of the object indicates that a position or shape of the target region to be treated is changed. In some embodiments, the parameter(s) may be preset in the treatment plan.

In some embodiments, the MLC 400 may include one or more leaves configured to assume discrete positions. In some embodiments, the MLC 400 may include one or more leaves that are "binary" in that the leaves may assume only closed (i.e., radiation-shielding) and open (i.e., radiation-transmitting) states. Such an MLC including "binary" leaves may be referred to as a binary MLC. In some embodiments, the MLC 400 may include one or more leaves 410 configured to move between at least two positions and be parked at a position along its trajectory of movement. In some embodiments, one or more of the at least two positions may be adjustable. In some embodiments, the at least two positions may be determined or adjusted by the processing device 140. In some embodiments, each leaf 410 may have a closed position (or radiation-shielding position) and an open position (or radiation-transmitting position). If a leaf is at its closed position, the passage of a radiation beamlet of the radiation beam may be blocked. If a leaf is at its open position, the passage of a radiation beamlet of the radiation beam may be permitted. The leaves 410 at their corresponding open positions may form an aperture, such that the radiation beam (e.g., the radiation beam emitted from the radiation delivery device 110) may pass through the aperture and reach the treatment region of the object to perform the RT. In some embodiments, the closed position and/or the open position of a leaf may be adjustable according to the treatment plan. For instance, a leaf may have multiple open positions that may facilitate to define one or more aperture shapes.

In some embodiments, the MLC 400 may include two opposing banks arranged in a same level (i.e., a same plane). A plurality of leaves may be arranged in the two opposing banks and/or form a plurality of leaf pairs. A leaf pair may refer to two leaves that are arranged in the two opposing banks, respectively, and are longitudinally movable relative to each other along the X-axis direction as illustrated in FIG. 4. In some embodiments, the longitudinal moving direction may be traversed to a beam direction (along the Z-axis direction as illustrated in FIG. 4). In some embodiments, one leaf of a leaf pair in a bank may be longitudinally movable relative to the other leaf of the pair in the opposing bank. In some embodiments, one or more leaf pairs that are not a portion of the leaf pairs forming the aperture shape may be closed and form one or more closed leaf pairs. The closed leaf pair(s) may be configured to block at least a portion of the radiation beam impinging thereon. In some embodiments, a gap may exist between the leaves of a closed leaf pair where the leaves meet. At least a portion of the radiation beam impinging on the closed leaf pair may leak through the gap. In some embodiments, the position of a closed leaf pair may be adjusted such that the position of the gap between the leaves of the closed leaf pair is adjusted. In some embodiments, if one or more of the closed leaf pairs, or a portion thereof (e.g., a gap between the leaves of each of the one or more closed leaf pairs) are covered by a jaw, the one or more of the closed leaf pairs may be kept still without position adjustment.

The drive mechanism(s) 430 may be configured to actuate one or more of the leaves 410 to move. In some embodiments, the drive mechanism(s) 430 may facilitate the movement of the leaves 410 such that the MLC 400 can translate the leaves 410 between a first aperture shape and a second aperture shape. In some embodiments, each leaf 410 may be capable of translating between a first position and a second position (e.g., from an open position to a closed position, from a closed position to an open position, from a first open position to a second open position, from a first closed position to a second closed position). In some embodiments, each leaf 410 may be actuated to move independently or separately from other leaves 410 of the MLC 400. In some embodiments, two or more leaves 410 may be actuated to move simultaneously. More descriptions of the adjustment of the position(s) of the leaves 410 may be found elsewhere in the present disclosure (e.g., FIGS. 5A-8B and descriptions thereof).

In some embodiments, the drive mechanism(s) 430 may include a hydraulic drive mechanism, a spring-based drive mechanism, an electric-charge-based drive mechanism, a magnetic drive mechanism, a pneumatic drive mechanism, or the like, or a combination thereof. In some embodiments, the drive mechanism(s) 430 may include a plurality of driving motors. In some embodiments, a driving motor may actuate one or more leaves 410 to move. In some embodiments, the drive mechanism 430 may include a drive screw operably coupled to a driving motor to transmit a driving force generated by the driving motor to a corresponding leaf. The drive mechanism(s) 430 may move each leaf of the MLC 400 individually and/or independently, or may move two or more leaves together.

In some embodiments, the MLC 400 may include a plurality of the leaves 410, for example, 12, 15, 16, 24, 25, 31, 32, 36, 48, 50, 64, 72, 75, 100, 101, 120, 128, 135, etc. Merely by way of example, the MLC 400 may include 64 leaves. In some embodiments, each leaf 410 of the MLC 400 may have a width of about 1 mm to about 10 mm (e.g., about 2 mm). In some embodiments, the travel length of each leaf may be from about 0.25 cm to about 3 cm (e.g., about 1 cm). The smaller the travel range of the leaves 410 of the MLC 400 is, the more precise an aperture defined by the MLC 400 may be, and the more precisely the radiation may be delivered. However, in some embodiments, reducing leaf travel length and/or width may prolong patient treatment time. The size and shape of the leaves 410 may be at least partially determined by the geometry of a gantry, the width of the radiation beam, and/or the desired "resolution" at which radiation is to be applied (e.g., leaf width, number (or count) of leaves). The depth (or height) of the leaves 410 may be sufficiently thick to impede the transmission of the radiation beam when the leaves 410 are in the closed position. The depth of a leaf 410 may be the dimension of the leaf 410 along the Z-axis direction as illustrated in FIG. 4.

In some embodiments, the speed of a leaf movement may be increased by increasing the speed of the drive mechanism(s) 430. Alternatively or additionally, the MLC 400 may optionally use reduced-weight leaves. In some embodiments, only a portion of the leaves 410 that shield the radiation beam may have a high atomic number material (e.g., tungsten), while the peripheral support structure(s) of the leaves 410 may include one or more lighter-weight materials. In some embodiments, a portion of a leaf 410 may be made of a substantially-radiation-impermeable material (e.g., tungsten), while the remaining portion of the leaf 410 may be made of one or more other materials (e.g., a material that is less dense and/or lighter than the substantially-radiation-impermeable material, such as stainless steel or titanium). In some embodiments, the portion of the leaf 410 made of a substantially-radiation-impermeable material may also be referred to as a substantially-radiation-impermeable portion of the leaf 410. In some embodiments, removing or hollowing out one or more regions of the leaf 410 may help to reduce the weight of the leaf 410 with little or no impact on the ability of the leaf 410 to impede radiation transmission. For example, a first section of the substantially-radiation-impermeable portion of the leaf 410 that is in the radiation path may be substantially solid, while a second section of the substantially-radiation-impermeable portion of the leaf 410 that is not in the radiation path may have one or more hollow regions.

In some embodiments, as shown in FIG. 4, the X-axis direction may refer to the longitudinal moving direction (as indicated by the arrow A) of the leaves of the MLC, the Y-axis direction may refer to the arrangement direction of adjacent leaves in a same bank of the MLC, and the Z-axis direction may be perpendicular to the X-axis direction and the Y-axis direction. In some embodiments, the X-axis direction and the Y-axis direction may be traversed to the beam direction. It should be noted that the X-axis direction, Y-axis direction, and Z-axis direction in the present disclosure are defined relative to the MLC. If the MLC rotates with the gantry, the actual direction of the X-axis direction, Y-axis direction, and Z-axis direction relative to the radiation delivery device 110 may change with the rotation of the MLC. In some embodiments, the longitudinal moving direction of the leaves may be indicated by the arrow A, i.e., the X-axis direction as shown in FIG. 4.

Figure 5A:
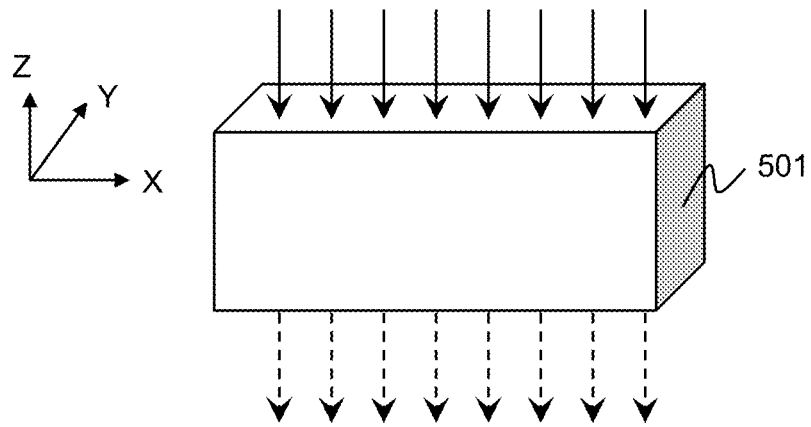
FIGS. 5A-5D are schematic diagrams illustrating exemplary leaf gap leakage of radiation according to some embodiments of the present disclosure.
Figure 5B:
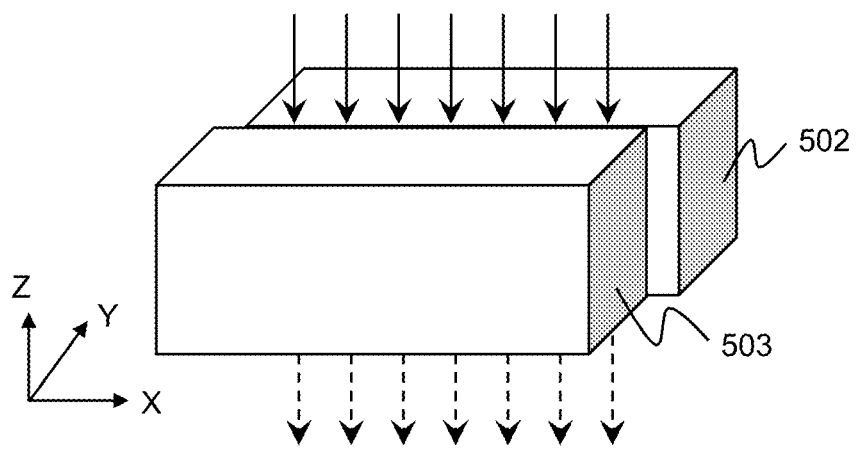
Figure 5C:
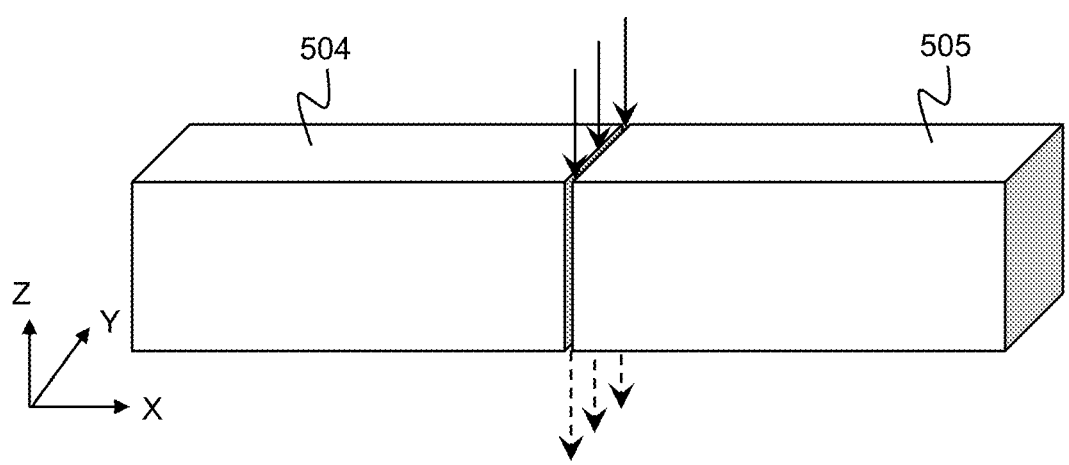
Figure 5D:
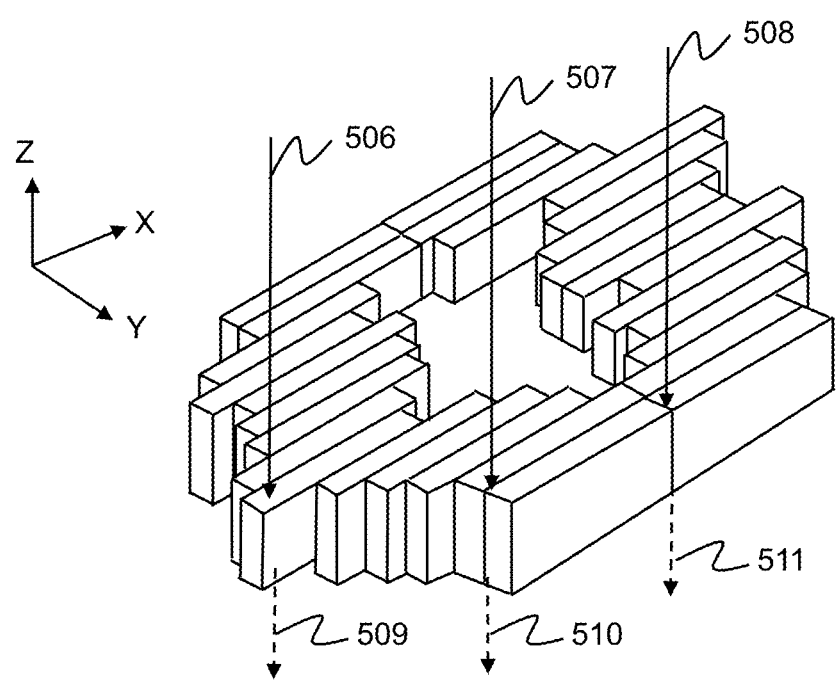

FIGS. 5A-5D are schematic diagrams illustrating exemplary leaf gap leakage of radiation according to some embodiments of the present disclosure. FIG. 5A is a schematic diagram illustrating a first leakage through a leaf. FIG. 5B is a schematic diagram illustrating a second leakage between two adjacent leaves. FIG. 5C is a schematic diagram illustrating a third leakage between a closed leaf pair. FIG. 5D is a schematic diagram illustrating three types of leaf gap leakage.

In some embodiments, the terms of "length," "width," "height," "side," and "end" of a leaf may be used in the description of the MLC and radiation leakage effects. The "length" of a leaf as used herein may refer to a leaf dimension (e.g., in the X-axis direction) that is parallel to the leaf moving direction. The "width" of a leaf may refer to a dimension of the leaf (e.g., in the Y-axis direction) that is traverse to the leaf moving direction and the direction of the radiation beam. The "height" of a leaf may refer to a dimension of the leaf (e.g., in the Z-axis direction) substantially along the radiation beam direction. The "side" of a leaf may refer to a surface of the leaf (e.g., in the XZ plane) facing a neighboring leaf in a same bank. The "end" of a leaf may refer to a surface of the leaf (e.g., in the YZ plane) at an end of the leaf along the length of the leaf.

In some embodiments, the leaves of the MLC exemplified in FIGS. 5A-5D may have an rectangular shape. It should be noted that the rectangular cubes in FIGS. 5A-5D are merely provided for the purposes of illustration, and not intended to limit the scope of the leaf in the present disclosure. In some embodiments, the leaves in the MLC may have a substantially same cross-section (e.g., a cross-section in the YZ plane). For example, the leaves in the MLC may have a same trapezoidal cross-section. The cross-section of the leaves may have other shapes including, for example, a rectangular shape, a tilted trapezoid shape, or a trapezoid with stepped or wavy side, or the like. In some embodiments, the pattern of cross-sections of the leaves may alternate, such as trapezoid, rectangle, trapezoid, rectangle, and so on. In some embodiments, the leaf side surfaces may be flat. In some embodiments, the neighboring leaf side surfaces may form a gap or spacing ranging from approximately 10 to 100 micrometers to facilitate relative movement between the leaves. In some embodiments, the leaf side gaps may be substantially the same. In some embodiments, the leaf end may be round, flat, or in one of various other configurations.

A first leakage through a leaf is shown in FIG. 5A. The arrows shown in FIG. 5A illustrate a radiation beam. A radiation beam may be emitted from a radiation source. A radiation beam may include a plurality of radiation beamlets. In some embodiments, the solid arrows may indicate the radiation beam delivered from a radiation source to the leaf 501. In some embodiments, the dashed arrows may indicate the first leakage though the leaf 501. The radiation beam may include a particle beam, a photon beam, an ultrasound beam (e.g., a high intensity focused ultrasound beam), or the like, or a combination thereof. The particle beam may include a stream of neutrons, protons, electrons, heavy ions, or the like, or a combination thereof. The photon beam may include an X-ray beam, a γ-ray beam, an α-ray beam, a β-ray beam, an ultraviolet beam, a laser beam, or the like, or a combination thereof. It should be noted that the incidence direction of the radiation beam perpendicular to the XY-plane in FIG. 5A is merely provided for the purposes of illustration, and not intended to limit the scope of the present disclosure. For example, in some embodiments, the incidence direction of the radiation beam may form a certain angle with the XY-plane, such as 15°, 30°, 45°, 60°, 75°, or the like. In some embodiments, the first leakage may be due to a relatively slight radiolucency of the leaf 501. In some embodiments, the first leakage may relate to the leaf material and/or the leaf height. For example, the first leakage may be a function of the leaf material and/or the leaf height. In some embodiments, the material of the leaf may include a high atomic number material (e.g., tungsten) which can block the radiation beam. In some embodiments, only a portion of the leaves that shield the radiation beam may have a high atomic number material (e.g., tungsten), while the peripheral support structure(s) of the leaves may include lighter-weight materials. In some embodiments, because the first leakage may be determined based on the leaf material and the leaf height, the first leakage can be maintained at an acceptable range. In some embodiments, the first leakage may be relatively small.

A second leakage between adjacent leaves of a same bank is shown in FIG. 5B. The arrows shown in FIG. 5B illustrate a radiation beam. In some embodiments, the solid arrows may indicate the radiation beam delivered from a radiation source to the leaves 502 and 503. In some embodiments, the dashed arrows may indicate the second leakage between the adjacent leaves 502 and 503. It should be noted that the incidence direction of the radiation beam perpendicular to the XY-plane in FIG. 5B is merely provided for the purposes of illustration, and not intended to limit the scope of the present disclosure. For example, in some embodiments, the incidence direction of the radiation beam may form a certain angle with the XY-plane, such as 15°, 30°, 45°, 60°, 75°, or the like. In some embodiments, the second leakage may be induced by the spacing between the adjacent leaves 502 and 503. In some embodiments, the second leakage may relate to the leaf geometry (e.g., a geometry of a side surface of the leaves) and/or mechanical precision of the leaves. For example, the second leakage may be a function of the leaf geometry and the mechanical precision. In some embodiments, the second leakage may be reduced by modifying the leaf geometry, for example, using a tongue and groove geometry.

A third leakage through a gap between leaves of a closed leaf pair is shown in FIG. 5C. The arrows shown in FIG. 5C illustrate a radiation beam. In some embodiments, the solid arrows may indicate the radiation beam delivered from a radiation source to a closed leaf pair including the leaves 504 and 505. In some embodiments, the dashed arrows may indicate the third leakage between the closed leaf pair. It should be noted that the incidence direction of the radiation beam perpendicular to the XY-plane in FIG. 5C is merely provided for the purposes of illustration, and not intended to limit the scope of the present disclosure. For example, in some embodiments, the incidence direction of the radiation beam may form a certain angle with the XY-plane, such as 15°, 30°, 45°, 60°, 75°, or the like. If a portion of the radiation beam needs to be blocked according to the treatment plan, one or more leaf pairs may be closed, so that the portion of the radiation beam may not pass through the closed leaf pair(s). In some embodiments, one or more leaf pairs may be closed to facilitate the formation of the aperture shape. However, in some embodiments, if the leaves of a closed leaf pair physically touch each other without any gap or spacing therebetween, the drive screws that move the leaf pair may seize up, resulting in damage to the drive mechanism. Therefore, touching of the opposing leaves of a leaf pair may need to be avoided. For example, a closed leaf pair may have a gap larger than 0.001 mm (e.g., 0.005 mm, 0.01 mm, 0.02 mm, 0.03 mm, 0.04 mm, 0.05 mm, etc.) to keep the drive screws performing normally. In some embodiments, the leaf end may be round, and accordingly, even though the leaves of the leaf pair physically touch each other, the third leakage may be present. In some embodiments, the third leakage may be relatively large in comparison with the first leakage and/or the second leakage.

In some embodiments, as shown in FIG. 5D, one or more types of leakage may be present during the radiation beam delivery. The arrows shown in FIG. 5D illustrate a radiation beam. In some embodiments, the solid arrows 506, 507, and 508 may refer to the radiation beam delivered from a radiation source to the leaves. In some embodiments, the dashed arrows 509, 510, and 511 may indicate the one or more types of leakage. It should be noted that the incidence direction of the radiation beam perpendicular to the XY-plane in FIG. 5D is merely provided for the purposes of illustration, and not intended to limit the scope of the present disclosure. For example, in some embodiments, the incidence direction of the radiation beam may form a certain angle with the XY-plane, such as 15°, 30°, 45°, 60°, 75°, or the like. In some embodiments, the leaf height may be large enough to reduce or eliminate the first leakage (i.e., the leakage through the leaves), and accordingly, the second leakage and/or the third leakage may be present. In some embodiments, the tongue and groove geometry may be introduced into the leaf geometry to reduce or eliminate the second leakage (i.e., the leakage between adjacent leaves), and accordingly, the first leakage and/or the third leakage may be present. In some embodiments, the leaf height may be large enough, and the tongue and groove geometry may be introduced to reduce or eliminate the second leakage, and accordingly, only the third leakage may be present.

In some embodiments, if one or more types of leakage are present, the leakage dose may be relatively large, or the leakage dose may be accumulated at a same spot, and damage may be introduced to health tissues. Therefore, it may be desirable to reduce or eliminate the effect of the leakages on the object. In some embodiments, the first leakage may be reduced or eliminated by using a high atomic number leaf material (e.g., tungsten, lead). In some embodiments, the first leakage may be reduced or eliminated by using leaves of a relatively large height. In some embodiments, the second leakage may be reduced or eliminated by using a tongue and groove geometry.

Figure 7:
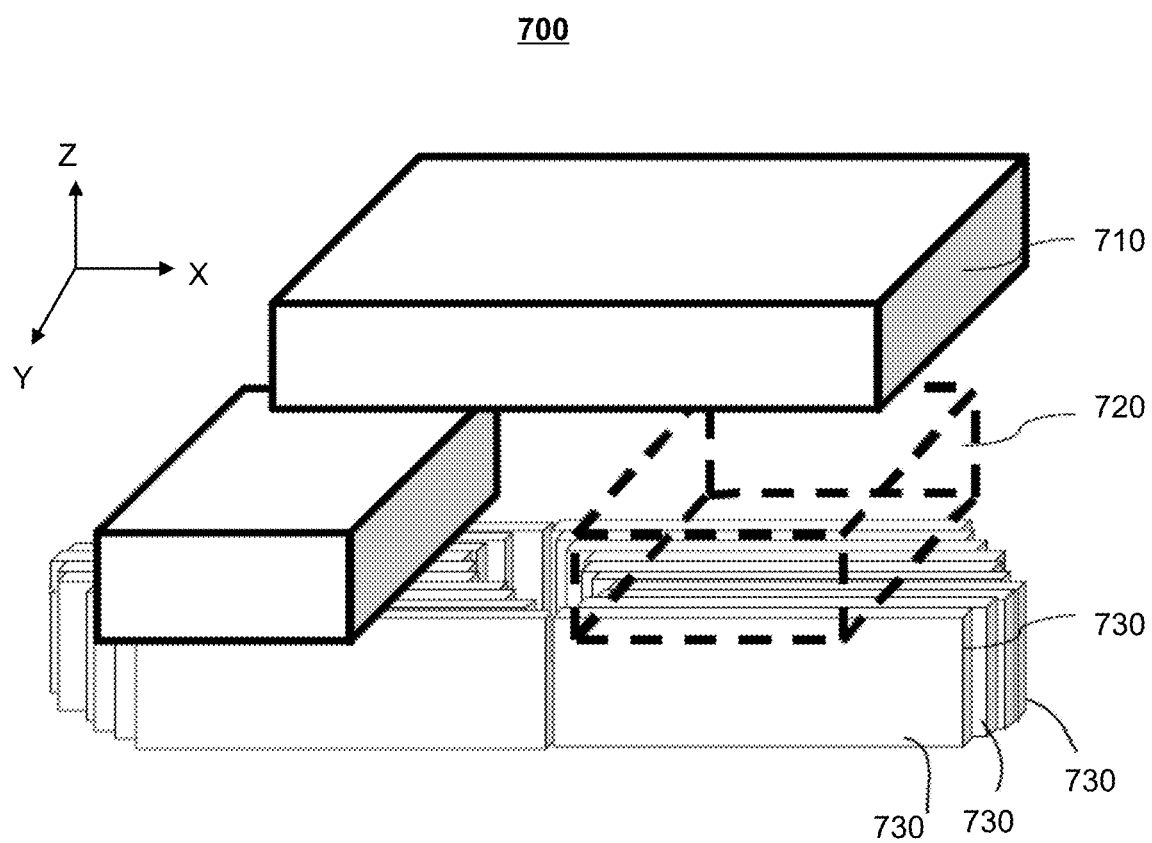
FIG. 7 is a schematic diagram illustrating an exemplary MLC with one or more jaws according to some embodiments of the present disclosure.

In some embodiments, the third leakage may be reduced or eliminated by covering the gap or spacing with one or more jaws (e.g., one or more Y jaws, and/or one or more X jaws as illustrated in FIG. 7). In some embodiments, the third leakage may be reduced or eliminated by moving the gap or spacing of the closed leaf pairs away from a central axis of the radiation beam to avoid a direct line of sight (from the radiation beam's point of view) through the leaf gaps. In some embodiments, the third leakage may be reduced or eliminated by closing the leaves as much as possible. In some embodiments, the effect of the third leakage may be reduced by computing the dose of the leakage through the leaf gap of the closed leaf pairs in the treatment planning system and/or positioning the leaf gap at a place in which a relatively small (e.g., the least) amount of damage to normal tissues (e.g., a critical organ) may occur.

In some embodiments, an adverse effect of the third leakage on the object may be reduced or eliminated by spreading the the gaps or spacings of the closed leaf pairs and avoiding positioning the gaps or spacings of the closed leaf pairs at a same location (e.g., a central axis of the radiation beam). In some embodiments, a random offset may be introduced to adjust the position(s) of the leaf gap(s) between the closed leaf pair(s). And accordingly, an accumulation of leakage in a particular spot may be avoided (i.e., hot spot(s) may be avoided). Additionally or alternatively, the adverse effect of the third leakage may be reduced by selectively positioning the leaf gap such that at least a portion of the third leakage is directed to tissue of a relatively higher tolerance to radiation (and the resultant damages) and away from tissue of a relatively lower tolerance to radiation (and the resultant damages) (e.g., tissue of a vital organ). In some embodiments, various mechanisms, including introducing random offsets to and/or selectively positioning leaf gaps of closed leaf pairs, may be used in combination with one or more of the methods mentioned above to reduce the leakage dose and/or the effect of the leakage. More descriptions of reducing the leaf gap leakage or the effect thereof may be found elsewhere in the present disclosure (e.g., FIGS. 6-10 and descriptions thereof).

FIGS. 6A-6D are schematic diagrams illustrating an exemplary adjustment process of position(s) of the leaf gap(s) of closed leaf pairs according to some embodiments of the present disclosure.

Figure 6A:
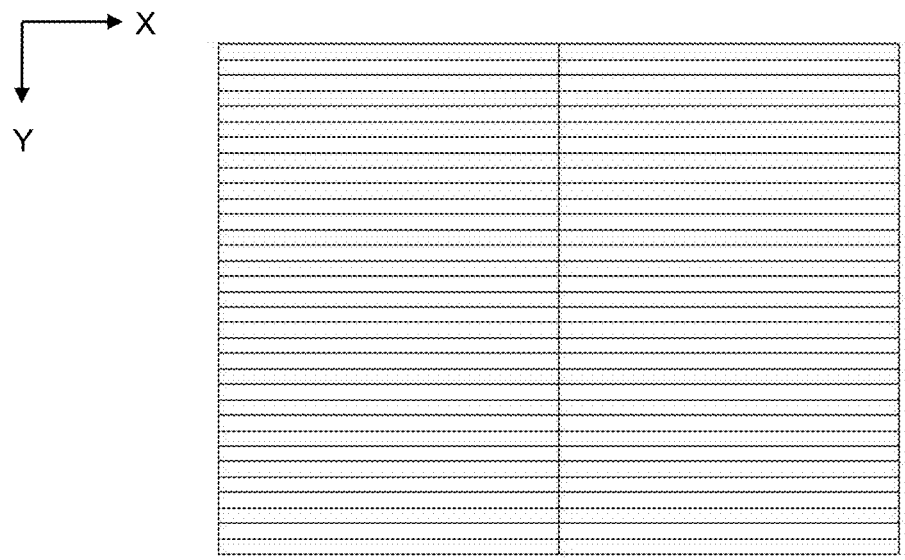
FIGS. 6A-6D are schematic diagrams illustrating an exemplary adjustment process of position(s) of the leaf gap(s) of closed leaf pairs according to some embodiments of the present disclosure.

FIG. 6A is a schematic diagram illustrating an exemplary closed status of leaf pairs of an MLC according to some embodiments of the present disclosure. As shown in FIG. 6A, one or more (e.g., all) of the leaf pairs of the MLC may be in a closed status and located at corresponding initial position(s). An initial position of a leaf pair may be the position that the leaf pair stays before a treatment process according to an initial configuration of the leaf pair.

Figure 6B:
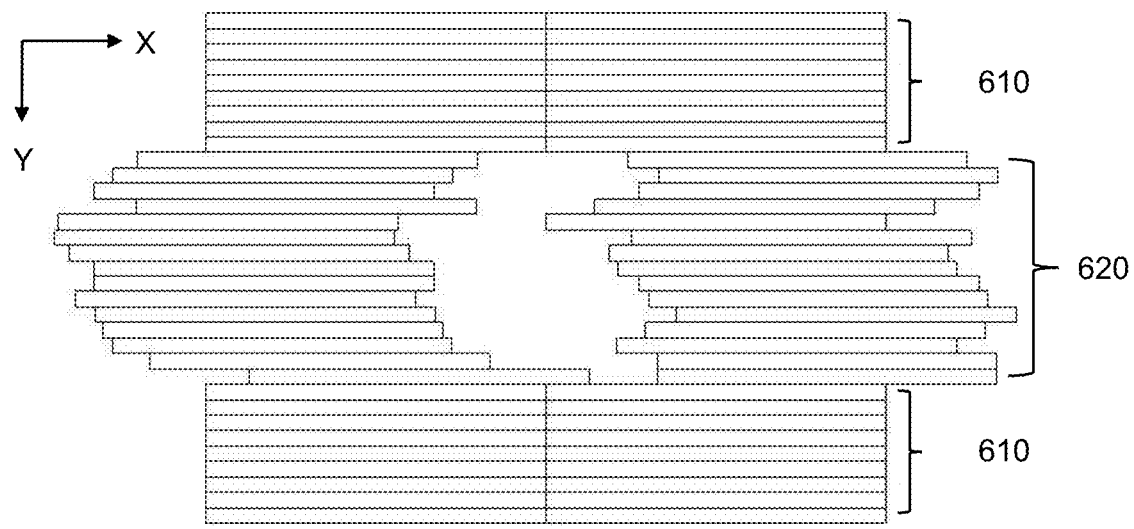

FIG. 6B is a schematic diagram illustrating an exemplary aperture shape formed by a portion of the leaf pairs of the MLC as provided by a treatment planning system according to some embodiments of the present disclosure. The treatment planning system may be configured to generate a treatment plan and/or optimize the dose distribution of the radiation before a treatment process starts. As shown in FIG. 6B, in some embodiments, a first portion of leaf pairs 620 may be caused (e.g., by the control module 904) to move to first prescribed positions and form a prescribed aperture shape (or a first aperture shape) according to a treatment plan. The first portion of leaf pairs 620 are also referred to as open leaf pairs 620. In some embodiments, the first aperture shape may be conformal with the treatment region of the object. In some embodiments, a second portion of leaf pairs 610 may stay at their respective initial positions, and radiation may be substantially blocked by the second portion of leaf pairs 610. The second portion of leaf pairs 610 may also be referred to as closed leaf pairs 610. The open leaf pairs 620 and the closed leaf pairs 610 in FIG. 6B may illustrate an original leaf status determined according to a treatment plan. As illustrated above, leakage of radiation through the leaf gaps of the closed leaf pairs 610 may be present during the beam delivery.

Figure 6C:
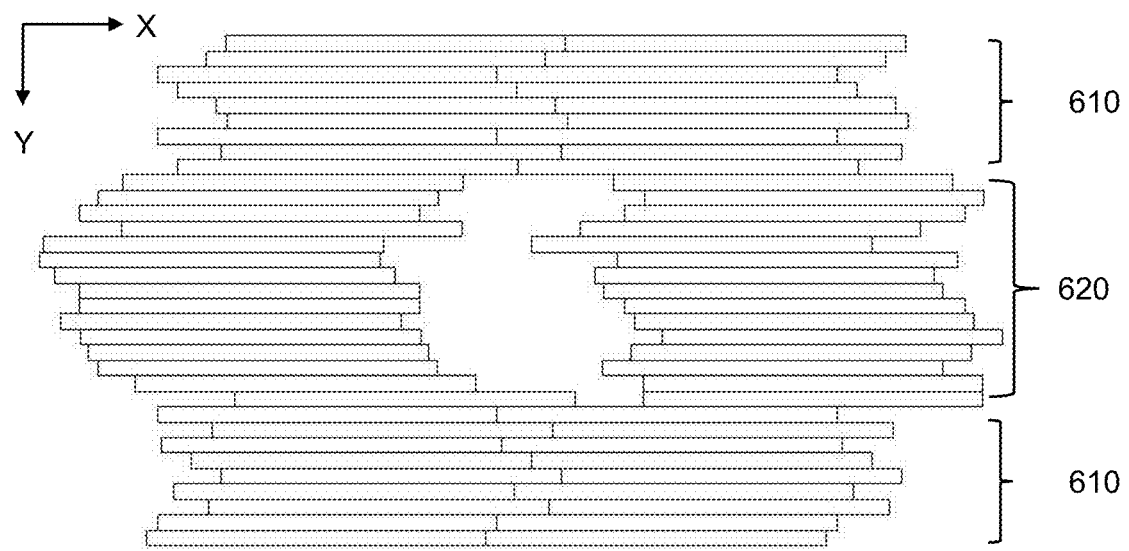

FIG. 6C is a schematic diagram illustrating an examplary configuration of adjusted closed leaf pairs of the MLC in a first treatment fraction (or treatment session) according to some embodiments of the present disclosure. As shown in FIG. 6C, in some embodiments, in the first treatment fraction, the open leaf pairs 620 may remain in an open status to form the first aperture shape. In some embodiments, before, at, or after the beginning of the first treatment fraction, one or more pairs of the closed leaf pairs 610 may be caused to move to first adjusted positions. In some embodiments, the positions of the one or more pairs of the closed leaf pairs 610 may be randomly adjusted by causing each of the one or more pairs of the closed leaf pairs 610 to move by a random offset. In some embodiments, the one or more random offsets may have random value(s) generated by a random number generator (e.g., pseudo random numbers). In some embodiments, at least two of the random offsets may be of a same value. In some embodiments, at least two of the random offsets may be of different values.

In some embodiments, a position of a closed leaf pair may be described by the position of the gap or spacing between the closed leaf pair (e.g., a centerline of the gap between the closed leaf pair) along the longitudinal moving direction of the closed leaf pair, considering that the dimension of each of the leaves of the closed leaf pair is known. In some embodiments, an adjustment of a position of a closed leaf pair may refer to that the two leaves of the closed leaf pair are moved along the longitudinal moving direction to adjust the position of the gap or spacing between the closed leaf pair. In some embodiments, the two leaves of the closed leaf pair may be caused to move by a same distance and/or along a same direction. For example, both the two leaves may be caused to move 1 cm along the positive direction of the X-axis. As another example, both the two leaves may be caused to move 1.5 cm along the negative direction of the X-axis. In some embodiments, the two leaves of the closed leaf pair may be caused to move simultaneously. For example, if the two leaves are caused to move when a radiation beam is on, then the two leaves may be caused to move simultaneously. In some embodiments, the two leaves of the closed leaf pair may be caused to move at different times (e.g., in sequence) to simplify the mechanical control and/or avoid physical touching of the leaves of the closed leaf pair. For example, during beam off, if a first leaf of the closed leaf pair is positioned in the positive direction of the X-axis relative to a second leaf of the closed leaf pair, then the first leaf may be firstly caused to move 1 cm along the positive direction of the X-axis, and then the second leaf of the closed leaf pair may be caused to move 1 cm along the positive direction of the X-axis. Alternatively, the second leaf may be firstly caused to move 0.5 cm along the negative direction of the X-axis, and then the first leaf may be caused to move 0.5 cm along the negative direction of the X-axis. In some embodiments, the relative position of the two leaves of the closed leaf pair may remain unchanged. That is, a size of the leaf gap between the closed leaf pair may remain unchanged.

In some embodiments, in a same treatment fraction, the position offsets (or offsets for brevity) for different closed leaf pairs may be the same or different, and the moving directions of different closed leaf pairs may be the same or different. In some embodiments, in different treatment fractions, the position offsets for a same closed leaf pair may be the same or different, and the moving directions of the same closed leaf pair may be the same or different. For example, in the first treatment fraction, a first closed leaf pair may be caused to move by a first position offset, and a second closed leaf pair may be caused to move by a second position offset, and accordingly, the first position offset and the second position offset may be the same or different.

Figure 6D:
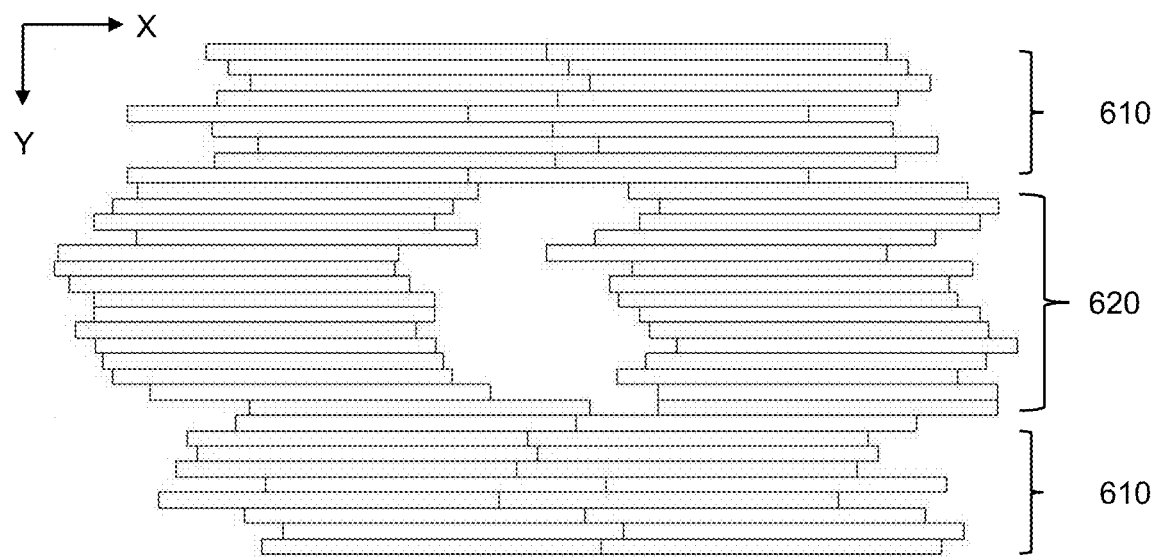

FIG. 6D is a schematic diagram illustrating an exemplary configuration of adjusted closed leaf pairs of the MLC in a second treatment fraction (or treatment session) according to some embodiments of the present disclosure. As shown in FIG. 6D, in some embodiments, in the second treatment fraction, one or more leaves of the open leaf pairs 620 may remain in an open status to form a second aperture shape. In some embodiments, the second aperture shape may be the same as the first aperture shape. Alternatively, the second aperture shape may be different from the first aperture shape. If the second aperture shape is different from the first aperture shape, one or more leaves of the open leaf pairs 620 may be caused to move to second prescribed positions, and/or one or more leaves of the closed leaf pairs 610 may become open leaf pair(s) 610. In some embodiments, the leaves of an open leaf pair 620 (at the first treatment fraction), by moving to their respective second prescribed positions, may become a closed leaf pair 620 in the second treatment fraction. In some embodiments, the leaves of an open leaf pair 620 (at the first treatment fraction), by moving to their respective second prescribed positions, may remain open but at least one of the leaves may be at a different position compared to its position in the first treatment fraction, and/or the gap formed by the open leaf pair 620 may be positioned differently compared to the gap formed by the same open leaf pair 620 in the first treatment fraction, and/or the size of the gap formed by the open leaf pair 620 may be different compared to the size of the gap formed by the same open leaf pair 620 in the first treatment fraction. In some embodiments, before, at, or after the beginning of the second treatment fraction, one or more pairs of the closed leaf pairs 610 may be caused to move to second adjusted positions. In some embodiments, the positions of the one or more pairs of the closed leaf pairs 610 may be randomly adjusted. In some embodiments, in the second treatment fraction, a third closed leaf pair may be caused to move by a third position offset, and a fourth closed leaf pair may be caused to move by a fourth position offset, and accordingly, the third position offset and the fourth position offset may be the same or different. In some embodiments, at least one of the closed leaf pairs 610 may remain at the same position in the second treatment fraction as in the first treatment fraction. In some embodiments, at least one of the closed leaf pairs 610 may remain closed in the second treatment fraction as in the first treatment fraction, but move by a distance, from the positions of the leaves of the at least one of the closed leaf pairs 610 in the first treatment fraction, to adjust the position of the gap of the at least one of the closed leaf pairs 610.

In some embodiments, because the positions of the closed leaf pairs are adjusted in the treatment fractions, a distribution of the leakage through the leaf gaps of the closed leaf pairs may be substantially homogenous, and the accumulation of the leaf gap leakage may be reduced. It should be noted that the above description of position adjustment of closed leaf pairs is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, a leaf pair may be open in a previous treatment fraction (or treatment session), and may be closed in a next treatment fraction (or treatment session). The position of the leaf pair may be adjusted as illustrated in FIGS. 6C and 6D after the leaf pair is closed. As another example, a leaf pair may be closed in a previous treatment fraction (or treatment session), and may be open in a next treatment fraction (or treatment session). The position of the leaf pair may be adjusted as illustrated in FIGS. 6C and 6D prior to opening the leaf pair. More descriptions of the adjustment of the closed leaf pairs may be found elsewhere in the present disclosure (e.g., FIG. 10 and descriptions thereof).

FIG. 7 is a schematic diagram illustrating an exemplary MLC with one or more jaws according to some embodiments of the present disclosure. As shown in FIG. 7, the MLC 700 may include one or more X jaws 720, one or more Y jaws 710, and a plurality of leaves 730. In some embodiments, the MLC 700 may have only the X jaw(s) 720 and the plurality of leaves 730, without any Y jaw(s) 710. In some embodiments, the MLC 700 may have only the Y jaw(s) 710 and the plurality of leaves 730, without any X jaw(s) 720. In some embodiments, the MLC 700 may have only the plurality of leaves 730, without any X jaw(s) 720 or Y jaw(s) 710. In some embodiments, the X jaw(s) 720 (if present) and the Y jaw(s) 710 (if present) may be positioned on different planes.

In some embodiments, the plurality of leaves 730 may be arranged in two banks or arrays to form a plurality of pairs of opposing leaves. In some embodiments, each leaf of a pair in a bank may be longitudinally movable (e.g., in the X-axis direction) relative to the other leaf of the pair in the opposing bank. In some embodiments, the leaves 730 may be similar to the leaves 410. More descriptions of the leaves may be found elsewhere in the present disclosure (e.g., FIG. 4 and descriptions thereof).

In some embodiments, the X jaw(s) 720 may be positioned in a lower plane relative to the Y jaw(s) 710 in the Z-axis direction. In some embodiments, the X jaw(s) 720 may move along the X-axis direction in a certain travel range. The certain travel range may relate to the configuration of the MLC 700. Merely by way of example, the certain travel range may be 50 cm. For example, an X jaw 720 can move 50 cm along the X-axis direction if an initial position of the X jaw 720 is located at one end of a travel path. As another example, an X jaw 720 can move 25 cm along the X-axis direction to an end of the travel path if an initial position of the X jaw 720 is located at the midpoint of the travel path. It should be noted that the travel range of 50 cm is merely provided for the purposes of illustration, and not intended to limit the scope of the present disclosure. In some embodiments, the X jaw 720 may have a high atomic number material (e.g., tungsten, lead). If the X jaw(s) 720 are present, one or more gaps of the closed leaf pairs may be covered by the X jaw(s) 720, and accordingly, the leaf gap leakage of the closed leaf pairs may be reduced or eliminated. In some embodiments, because of the maximum travel range of the X jaw(s) 720 and/or a maximum travel range of the closed leaf pairs, a portion of the leaf gaps of the closed leaf pairs may not be covered by the X jaw(s) 720, and accordingly, the leaf gap leakage of the closed leaf pairs may not be reduced or eliminated effectively by the X jaw(s) 720.

In some embodiments, the Y jaw(s) 710 may be positioned in an upper (or lower) plane relative to the X jaw(s) 720 in the Z-axis direction. In some embodiments, the Y jaw(s) 710 may move along the Y-axis direction in a certain travel range. The certain travel range may relate to the configuration of the MLC 700. In some embodiments, the certain travel range may be 50 cm. For example, a Y jaw 710 can move 50 cm along the Y-axis direction if an initial position of the Y jaw 710 is located at one end of a travel path. As another example, a Y jaw 710 can move 25 cm along the Y-axis direction to an end of the travel path if an initial position of the Y jaw 710 is located at the midpoint of the travel path. It should be noted that the travel range of 50 cm is merely provided for the purposes of illustration, and not intended to limit the scope of the present disclosure. In some embodiments, the Y jaw 710 may have a high atomic number material (e.g., tungsten, lead). If the Y jaw(s) 710 are present, one or more gaps of the closed leaf pairs may be covered by the Y jaw(s) 710, and accordingly, the leaf gap leakage of the closed leaf pairs may be reduced or eliminated. In some embodiments, because of the maximum travel range of the Y jaw(s) 710 and/or a maximum travel range of the closed leaf pairs, a portion of the leaf gaps of the closed leaf pairs may not be covered by the Y jaw(s) 710, and accordingly, the leaf gap leakage of the closed leaf pairs may not be reduced or eliminated effectively by the Y jaw(s) 710.

Figure 8A:
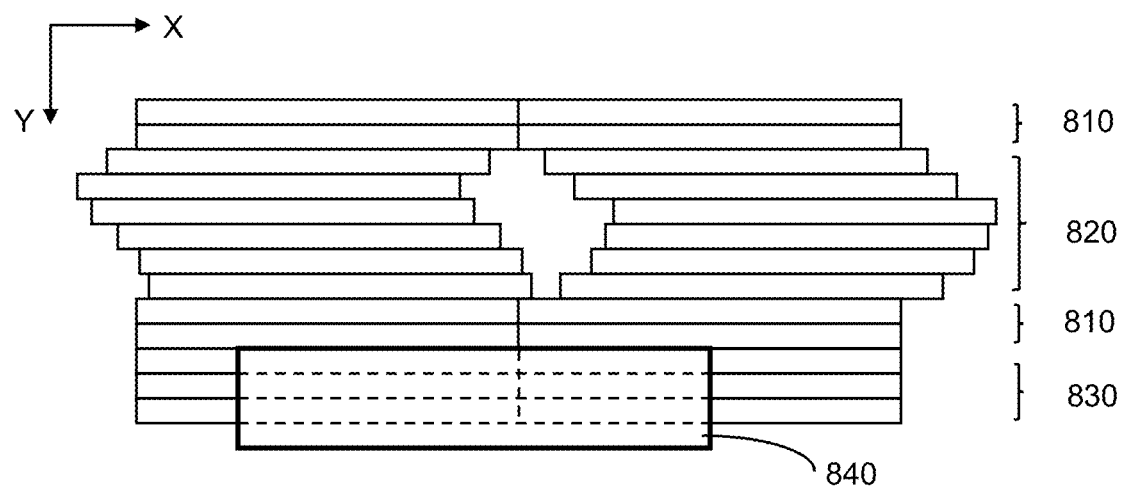
FIGS. 8A and 8B are schematic diagrams illustrating an exemplary adjustment process of a position of a leaf gap of a closed leaf pair in the presence of a jaw according to some embodiments of the present disclosure.
Figure 8B:
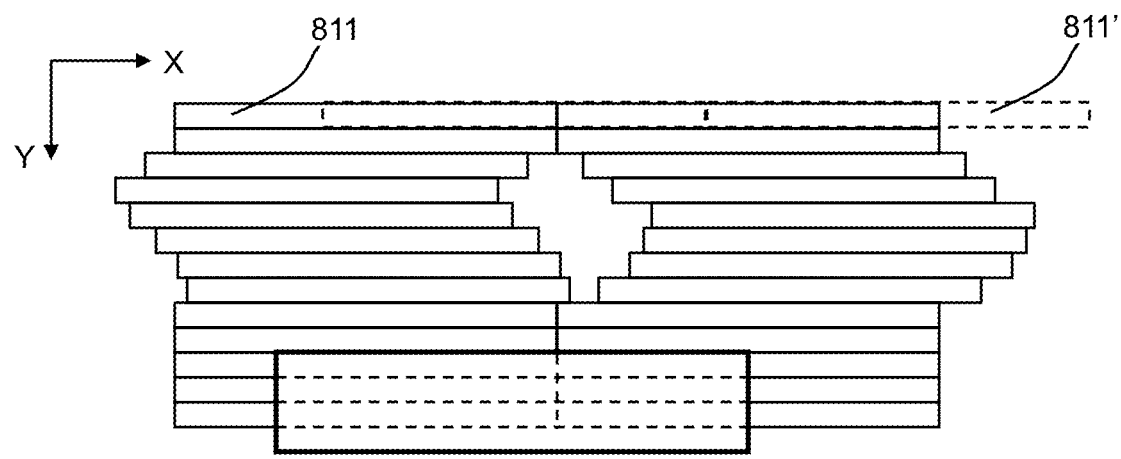

FIGS. 8A and 8B are schematic diagrams illustrating an exemplary adjustment process of a position of a leaf gap of a closed leaf pair in the presence of a jaw according to some embodiments of the present disclosure.

As shown in FIG. 8A, in a treatment process, a plurality of leaf pairs of an MLC may include one or more closed leaf pairs 810 and one or more open leaf pairs 820. In some embodiments, a portion of the closed leaf pairs 810 may not be covered by any jaw. In some embodiments, a portion of the closed leaf pairs may be covered by a jaw 840 (see the closed leaf pairs 830). In some embodiments, the open leaf pairs 820 may be caused to move to form a prescribed aperture shape. In some embodiments, the leaf gap leakage of the closed leaf pairs 830 may be blocked by the jaw 840, and thus, the leaf gap leakage of the closed leaf pairs 830 may be reduced or eliminated. In some embodiments, because the closed leaf pairs 810 are not covered by the jaw 840, the leaf gap leakage dose of the closed leaf pairs 810 may remain unchanged regardless of the presence (or absence) of the jaw 840. In some embodiments of the present disclosure, position(s) of one or more of the closed leaf pairs 810 that are not covered by any jaw may be adjusted. That is, one or more of the closed leaf pairs 810 that are not covered by any jaw may be caused to move to adjusted position(s), as illustrated in FIGS. 6C and 6D. As shown in FIG. 8B, an exemplary closed leaf pair 810 may be caused to move to an adjusted position. In some embodiments, a closed leaf pair may be caused to move from a current position (see the closed leaf pair 811) to an adjusted position (see the closed leaf pair 811'). In some embodiments, the positions of the closed leaf pairs 830 that are covered by the jaw 840 may remain unchanged (without position adjustment). In some embodiments, one or more of the closed leaf pairs 810 that are not covered by the jaw 840 may be moved to one or more adjusted positions before, at, or after one or more treatment fractions or beam deliveries. In some embodiments, the position(s) may be randomly adjusted. In some embodiments, the offsets of the closed leaf pairs to reach the randomly adjusted position(s) may be generated by a random number generator (e.g., pseudo random numbers). More descriptions of the determination of the randomly adjusted positions and the adjustment of the positions may be found elsewhere in the present disclosure (e.g., FIGS. 9-10 and descriptions thereof). In some embodiments, the jaw 840 may be absent, and the closed leaf pairs 830 may not be covered, and accordingly, one or more of the closed leaf pairs 830 may also be caused to move to adjusted positions similar to the closed leaf pairs 810. It should be noted that the adjustment of only one closed leaf pair 811 is described for the purposes of illustration, two or more (e.g., all) of the closed leaf pairs may be adjusted similarly. For persons having ordinary skills in the art, multiple variations and modifications may be made under the teachings of the present disclosure. However, those variations and modifications do not depart from the scope of the present disclosure.

Figure 9:
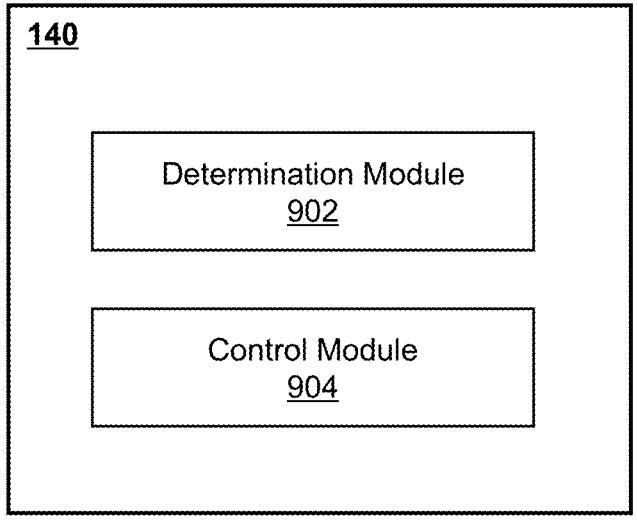
FIG. 9 is a block diagram illustrating an exemplary processing device according to some embodiments of the present disclosure.

FIG. 9 is a block diagram illustrating an exemplary processing device according to some embodiments of the present disclosure. The processing device 140 may include a determination module 902, and a control module 904.

In some embodiments, the determination module 902 may be configured to identify one or more closed leaf pairs. A closed leaf pair may refer to a leaf pair at a closed status. The closed leaf pair may have a gap or spacing therebetween. However, the gap or spacing between the closed leaf pair may lead to a third leakage. In some embodiments, the gaps of one or more closed leaf pairs may be covered by one or more jaws so that the third leakage of the covered closed leaf pair(s) can be reduced or eliminated. In some embodiments, the determination module 902 may identify one or more closed leaf pairs that are not covered by any jaw. In some embodiments, the determination module 902 may identify the closed leaf pair(s) according to a treatment plan or a portion thereof. More descriptions of the determination of one or more closed leaf pairs may be found elsewhere in the present disclosure (e.g., FIG. 10 and descriptions thereof).

Additionally or alternatively, the determination module 902 may be configured to determine one or more offsets for each of the identified one or more closed leaf pairs. In some embodiments, the determination module 902 may determine an offset based on a random value. In some embodiments, the determination module 902 may determine the offset(s) according to the current position(s) of the identified closed leaf pair(s) and/or the travel range(s) of the identified closed leaf pair(s). In some embodiments, the determination module 902 may determine the offsets for the closed leaf pairs in the treatment planning process, and accordingly, the treatment plan may further include the offsets. More description of the determination of one or more offsets for the one or more closed leaf pairs may be found elsewhere in the present disclosure (e.g., FIG. 10 and descriptions thereof).

In some embodiments, the control module 904 may be configured to cause the one or more closed leaf pairs to move based on the corresponding determined offsets. In some embodiments, the control module 904 may cause two leaves of a closed leaf pair to move, simultaneously or sequentially, by a same offset and/or along a same direction. More description of the movement of the one or more closed leaf pairs based on the corresponding determined offsets may be found elsewhere in the present disclosure (e.g., FIG. 10 and descriptions thereof).

Additionally or alternatively, the control module 904 may be configured to cause one or more open leaf pairs to move according to a treatment plan. More description of the movement of the one or more open leaf pairs according to the treatment plan may be found elsewhere in the present disclosure (e.g., FIG. 10 and descriptions thereof).

It should be noted that the above description of the processing device 140 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the determination module 902 may be divided into two units, and the closed leaf pair(s) and the offset(s) may be determined by two units respectively. As another example, the control module 904 may be divided into two units, and the closed leaf pair(s) and the open leaf pair(s) may be controlled respectively.

Figure 10:
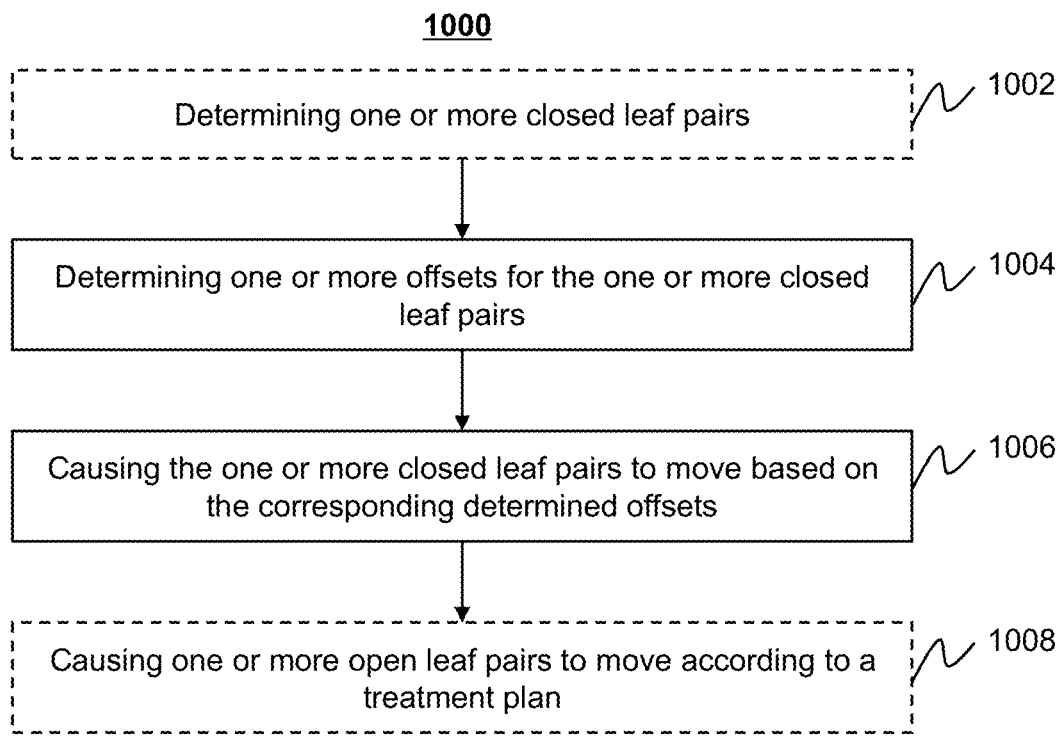
FIG. 10 is a flowchart illustrating an exemplary process for adjusting a multi-leaf collimator (MLC) according to some embodiments of the present disclosure.

FIG. 10 is a flowchart illustrating an exemplary process for adjusting a multi-leaf collimator (MLC) according to some embodiments of the present disclosure. In some embodiments, at least part of process 1000 may be performed by the processing device 140 (implemented in, for example, the computing device 200 shown in FIG. 2). For example, the process 1000 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 9). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1002, one or more closed leaf pairs of the multi-leaf collimator (MLC) may be identified. In some embodiments, the processing device 140 (e.g., the determination module 902) may perform operation 1002. A closed leaf pair may refer to a leaf pair at a closed status. The closed leaf pair may have a gap or spacing therebetween. As illustrated in FIG. 5C, the gap or spacing may be configured to prevent the closed leaf pair from physically touching each other, and/or keep the drive screw performing normally. However, the gap or spacing between the closed leaf pair may lead to a third leakage. More descriptions of the third leakage may be found elsewhere in the present disclosure (e.g., FIGS. 5C and 5D, and descriptions thereof). In some embodiments, the gaps of one or more closed leaf pairs may be covered by one or more jaws so that the third leakage of the covered closed leaf pair(s) can be reduced or eliminated. More descriptions of the jaws may be found elsewhere in the present disclosure (e.g., FIGS. 8A and 8B, and descriptions thereof). In some embodiments, one or more closed leaf pairs that are not covered by any jaw (e.g., one or more of the closed leaf pairs 810 illustrated in FIGS. 8A and 8B) may be identified. In some embodiments, the closed leaf pair(s) may be identified for further position adjustment (see operations 1004-1006).

In some embodiments, the closed leaf pair(s) may be identified according to a treatment plan or a portion thereof. In some embodiments, before a treatment process of an object starts, a treatment plan may be generated by a treatment planning system associated with the radiotherapy system 100. In some embodiments, the treatment plan may include information associated with the treatment process including, for example, one or more radiation parameters, a treatment dose, or the like, or a combination thereof. The radiation parameters may include radiation beam properties (e.g., a range, an aperture shape, an intensity, a radiation direction, or the like), positions and/or directions of an object, geometric properties of the MLC, or the like. In some embodiments, a treatment process may include one or more treatment fractions (or treatment sessions). In some embodiments, after the treatment plan is generated, a user may verify and/or adjust the treatment plan to avoid potential safety hazards and/or reduce the overall duration of a treatment process. In some embodiments, the user may include a doctor, a radiation therapist, a dosimetrist, a radiation oncologist, a radiation specialist, or the like.

Although the treatment plan may be determined before the treatment process, the closed leaf pair(s) may be determined before the treatment process or during the treatment process. In some embodiments, the closed leaf pair(s) may be identified at one time in the entire treatment process. Alternatively, the closed leaf pair(s) may be determined at different times in the entire treatment process. For example, after the treatment plan is generated and before the treatment process starts, the closed leaf pair(s) (e.g., closed leaf pair(s) that are not covered by any jaw) in one or more treatment fractions (or treatment sessions) may be already known according to the treatment plan, and then, the closed leaf pair(s) in the each of the one or more treatment fractions (or treatment sessions) of the entire treatment process may be identified at one time. As another example, during the treatment process (e.g., before each treatment fraction), one or more closed leaf pairs (e.g., closed leaf pair(s) that are not covered by any jaw) may be identified for an upcoming treatment fraction (or treatment session). In some embodiments, one or more first closed leaf pairs may be identified for a first treatment fraction (or treatment session) before the first treatment fraction (or treatment session) starts; one or more second closed leaf pairs may be identified for a second treatment fraction (or treatment session) after the first treatment fraction (or treatment session) is finished but before the second treatment fraction (or treatment session) starts. In some embodiments, the one or more first closed leaf pairs and the one or more second closed leaf pairs may be the same, partially different (at least one first closed leaf pair being also a second closed leaf pair, and at least one first closed leaf pair being not a second closed leaf pair), or totally different (no first closed leaf pair being a second closed leaf pair).

It should be noted that in some embodiments, the closed leaf pairs may include a first portion and/or a second portion. In some embodiments, the first portion of the closed leaf pairs may be closed throughout the treatment process. In some embodiments, the second portion of the closed leaf pairs may be closed for one or more treatment fractions (or treatment sessions). For example, a leaf pair may be open in a previous treatment fraction, and may be closed in a next treatment fraction. As another example, a leaf pair may be closed in a previous treatment fraction, and may be open in a next treatment fraction.

In 1004, for each of the identified one or more closed leaf pairs, an offset may be determined. In some embodiments, the processing device 140 (e.g., the determination module 902) may perform operation 1004.

In some embodiments, an offset may refer to a movement distance of a closed leaf pair along the longitudinal direction, or a change in the position of the gap (e.g., the centerline of the gap) of a closed leaf pair along the longitudinal direction (e.g., the X-axis direction illustrated in FIGS. 4-8B), with respect to an initial configuration of the closed leaf pair (see, e.g., FIG. 6A and the description thereof), or the current position of the closed leaf pair. In some embodiments, an offset may be determined based on a random value. In some embodiments, the random value may be generated by a random number generator (e.g., a pseudo random number). In some embodiments, the random value may be within the range of the movement distance of the closed leaf pair, and the random value may be directly designated as the offset. In some embodiments, the range of the movement distance of the closed leaf pair may be determined based on the travel range of the closed leaf pair, the current positions of the leaves, or the like, or a combination thereof. Relevant description may be found elsewhere in the present disclosure. See, e.g., FIG. 6C and the description thereof. In some embodiments, the travel range of the closed leaf pair may be determined based on the travel range of each leaf of the closed leaf pair. For instance, if the travel ranges of the leaves of a closed leaf pair are the same, the travel range of the closed leaf pair may be the same as the travel range of each leaf of the closed leaf pair. As another example, if the travel ranges of the leaves of a closed leaf pair are different, the travel range of the closed leaf pair may be the shorter one of the travel ranges of the leaves of the closed leaf pair. In some embodiments, the random value may be beyond the range of the movement distance of the closed leaf pair, and accordingly, the random value may be modified (e.g., by being multiplied by a coefficient) to fall within the range of the movement distance of the closed leaf pair and then may be designated as the offset. In some embodiments, the random value may include a positive number, a negative number, and/or zero. A positive number may refer that the closed leaf pair is caused to move along the positive direction of the X-axis, while a negative number may refer that the closed leaf pair is caused to move along the negative direction of the X-axis, or vice versa. A zero number may refer that the closed leaf pair remains at a current position. In some embodiments, before the determination of the offset(s) of the identified closed leaf pair(s), current position(s) of the identified closed leaf pair(s) may be determined. In some embodiments, the current position(s) of the identified closed leaf pair(s) may be determined by the position detection device(s) described in FIG. 1. In some embodiments, the offset(s) may be determined according to the current position(s) of the identified closed leaf pair(s) and/or the travel range(s) of the identified closed leaf pair(s). For instance, the current position of a closed leaf pair is away from its initial position, and a determined offset is a distance that the closed leaf pair needs to travel from its current position.

In some embodiments, each of the one or more closed leaf pairs (i.e., the closed leaf pair(s) determined in 1002) may be assigned with an offset. In some embodiments, the offsets for a same closed leaf pair in different treatment fractions (or beam deliveries) may be the same, partially different, or different. For example, a first offset of a first closed leaf pair in a first treatment fraction and a second offset of the first closed leaf pair in a second treatment fraction may be the same or different. In some embodiments, the offsets for different closed leaf pairs in the same treatment fraction (or beam delivery) may be the same, partially different, or different. For example, a third offset of a third closed leaf pair in a third treatment fraction and a fourth offset of a fourth closed leaf pair in the third treatment fraction may be the same or different.

In some embodiments, the offsets for one or more of the identified closed leaf pairs may be generated before or at a beginning of one or more treatment fractions of the treatment process. In some embodiments, the offsets for one or more of the identified closed leaf pairs may be generated before or at a beginning of a beam delivery of one or more treatment fractions (or treatment sessions) of the treatment process.

In some embodiments, the offset for a closed leaf pair may be set as no larger than an offset threshold. In some embodiments, the offset threshold may be determined by the radiotherapy system 100, or may be preset by a user or operator via the terminal(s) 130. The offset threshold may be determined based on a travel range of the closed leaf pair, the time need and/or available for the closed leaf pair to adjust its position by the offset, a current position of the closed leaf pair, a mechanical constraint, a safety consideration, or the like, or a combination thereof. For instance, the offset may be within a certain distance from the current position of a closed leaf pair. As another example, a prescribed position of a closed leaf pair after its movement by the offset may be such that the leakage through the gap of the closed leaf pair avoids a vital organ and takes into consideration of tissue tolerance to radiation. As a further example, the sum of the offsets of a certain number (or count) of closed leaf pairs or all the closed leaf pairs in an MLC whose positions are to be adjusted does not exceed a sum threshold. The mechanical constraint and/or the safety consideration may be determined by the radiotherapy system 100 automatically, by a user or operator manually, or semi-automatically with some user intervention in the determination performed by the system 100. The determination may be based on specifications of the devices within the system 100, one or more images of an object subject to a radiotherapy delivered by the system 100 (e.g., an image including anatomical information of the object to show where organs, different types of tissue, a lesion, etc., are located), other treatment related information of the object (e.g., health history of the object, treatment history of the object, etc.), or the like, or a combination thereof. In some embodiments, the treatment plan may further include the offset threshold, the mechanical constraints, a safety consideration, or the like, or a combination thereof.

In some embodiments, the offsets for the identified closed leaf pairs may be determined in the treatment planning process, and accordingly, the treatment plan may further include the offsets. In some embodiments, the offsets for the identified closed leaf pairs may be determined, in the treatment planning process, based on the positions of one or more leaf pairs of the MLC in each treatment field, the positions of one or more jaws in each treatment field, and/or the beam intensity in each treatment field, or the like. In some embodiments, one or more initial offsets of the identified closed leaf pairs may be determined. In some embodiments, the initial offset(s) may have predetermined value(s) or random value(s). In some embodiments, the initial offset(s) may be input into the treatment planning system, and one or more iterations may be performed to optimize the initial offsets and the radiation dose distribution, so that the radiation dose distribution is optimized, and a leakage distribution through the leaf gaps of the identified closed leaf pairs is substantially homogenous. The leakage distribution may refer to a distribution of the leakage dose throughout the treatment process. In some embodiments, to determine the leakage distribution through the leaf gaps of the closed leaf pairs, the dose leaking through the leaf gaps between the closed leaf pairs may be determined in the iterations, or a leaf gap leakage constant may be used. In some embodiments, the leaf gap leakage constant may have an empirical value.

Additionally or alternatively, in some embodiments, after the offsets are determined in the treatment planning process, the treatment plan may be evaluated or adjusted based on the leakage distribution to avoid potential safety hazards and/or ensure that the leakage distribution is substantially homogenous or acceptable. In some embodiments, an actual leakage distribution may be computed according to the treatment plan, and/or compared with a dose standard to ensure that the treatment plan is feasible. The dose standard may refer to an acceptable dose limitation that a healthy object can tolerate. It should be noted that if the offsets for the identified closed leaf pairs are determined in the treatment planning process, in addition to the open leaf pairs that have prescribed positions, the identified closed leaf pairs may also have prescribed positions.

In 1006, the one or more closed leaf pairs may be caused to move based on the corresponding determined offsets. In some embodiments, the processing device 140 (e.g., the control module 904) may perform operation 1006. A movement of a closed leaf pair may refer that the two leaves of the closed leaf pair are moved along the longitudinal moving direction to adjust the position of the gap or spacing between the closed leaf pair. In some embodiments, the two leaves of the closed leaf pair may be caused to move by a same offset and/or along a same direction. In some embodiments, the relative position of the two leaves of the closed leaf pair may remain unchanged, and accordingly, a size of the leaf gap between the closed leaf pair may remain unchanged.

In some embodiments, the radiation therapy may be static. That is, the open leaf pairs that form an aperture shape may be static during beam delivery. In some embodiments, one or more open leaf pairs may be caused to move (according to the treatment plan) to form an aperture shape before the beam delivery. In some embodiments, the radiation therapy may be dynamic. That is, one or more open leaf pairs that form the aperture shape may be moved during beam delivery. In some embodiments, the one or more identified closed leaf pairs may be caused to move, based on the one or more determined offsets, when the open leaf pairs are static (e.g., after or before the open leaf pairs are caused to move and form the aperture shape). In some embodiments, the identified closed leaf pairs may be caused to move before the beam delivery (or a treatment fraction). In some embodiments, the identified closed leaf pairs may be caused to move when the open leaf pairs are caused to move according to the treatment plan. In some embodiments, the identified closed leaf pairs may be caused to move (e.g., dynamically) by the corresponding offsets during the beam delivery. In one or more fractions, the one or more identified closed leaf pairs may be caused to move, based on the one or more determined offsets, dynamically during a beam delivery. In some embodiments, before or at the beginning of one or more treatment fractions (or beam deliveries), the identified closed leaf pairs may be caused to move based on the one or more determined offsets.

In some embodiments, a first closed leaf pair may be caused to move by a first offset in a first treatment fraction. In some embodiments, the first closed leaf pair may be caused to move by a second offset in a second treatment fraction. In some embodiments, the first offset and the second offset between different fractions may be different. In some embodiments, the first offset and the second offset between different fractions may be the same.

In some embodiments, a third closed leaf pair may be caused to move by a third offset in a third treatment fraction. In some embodiments, a fourth closed leaf pair may be caused to move by a fourth offset in the third treatment fraction. In some embodiments, the third offset and the fourth offset between different closed leaf pairs may be different. In some embodiments, the third offset and the fourth offset between different closed leaf pairs may be the same.

In 1008, one or more open leaf pairs may be caused to move according to a treatment plan. In some embodiments, the processing device 140 (e.g., the control module 904) may perform operation 1008. In some embodiments, the radiation therapy may be static, and accordingly, the one or more open leaf pairs may be caused to move, according to the treatment plan, to form an aperture shape before one or more treatment fractions (or beam deliveries). In some embodiments, the radiation therapy may be dynamic, and accordingly, the one or more open leaf pairs may be caused to move, according to the treatment plan, dynamically to change the aperture shape during one or more treatment fractions (or beam deliveries).

In some embodiments, a fifth leaf pair whose status is changed, according to the treatment plan, from open to closed, may be determined. If the fifth leaf pair needs to be closed at a time point in the treatment process, then the fifth leaf pair may be closed at a prescribed position. Afterwards, the fifth leaf pair may be caused to move by a corresponding offset as described in 1006. In some embodiments, a sixth leaf pair whose status is changed, according to the treatment plan, from closed to open, may be determined. In some embodiments, prior to opening the sixth leaf pair, the sixth leaf pair may be caused to move to a prescribed position according to the treatment plan. Afterwards, the sixth leaf pair may be caused to move from the prescribed position by a corresponding offset as described in 1006. In some embodiments, the fifth leaf pair and/or the sixth leaf pair may be determined as closed leaf pairs in 1002 when they are in a closed status.

It should be noted that the above description of the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 1002 and 1004 may be integrated into a single operation. As another example, operation 1008 may be performed before or simultaneously with one or more of operations 1002-1006. As a further example, operations 1002 and/or 1008 may be omitted. In some embodiments, the control module 904 may obtain the offsets of the closed leaf pairs, and/or identify the current positions of the closed leaf pairs. In some embodiments, the current position(s) of one or more closed leaf pairs may be obtained by the processing device 140 (e.g., the control module 904). In some embodiments, the processing device 140 (e.g., the determination module 902) may determine the offsets based on the current positions of the closed leaf pairs. In some embodiments, the processing device 140 (e.g., the control module 904) may cause the one or more closed leaf pairs to move from the current position(s) by the offset(s). If a closed leaf pair is moved, the processing device 140 (e.g., the control module 904) may update the current position of the closed leaf pair.

In some embodiments, as described in FIG. 4, the MLC may include two or more layers of leaves. In some embodiments, closed leaf pairs in different layers of the MLC may be caused to move according to respective offsets separately or independently. The offsets for the closed leaf pairs in different layers may be the same or different. In some embodiments, the offsets for the closed leaf pairs in different layers may be generated or adjusted separately or independently. In some embodiments, the offsets for the closed leaf pairs in different layers may be generated or adjusted according to one or more open leaf pairs in different layers. Merely by way of example, the MLC may include at least two layers of leaves. The at least two layers of leaves may include a first layer and a second layer, in which the first layer may include a first closed leaf pair, and the second layer may include a second closed leaf pair. In some embodiments, a first offset with a first random value and a second offset with a second random value may be generated or adjusted separately or independently. The first random value and the second random value may be the same or different. Accordingly, the first closed leaf pair in the first layer may be caused to move based on the first offset with the first random value, and the second closed leaf pair in the second layer may be caused to move based on the second offset with the second random value. In some embodiments, the leaf gaps between closed leaf pairs in different layers may be offset. Therefore, the leaf gap leakage through different layers may be effectively reduced. Additionally, by adjusting the closed leaf pairs in different layers, an accumulation of leakage dose in a specific spot (i.e., hot spot(s)) may be further avoided or mitigated.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation treatment method implemented on at least one machine, each machine having at least one processor and at least one storage device for adjusting a multi-leaf collimator (MLC), comprising:
    moving, according to a radiation treatment plan or a portion thereof, one or more leaves of the MLC, the MLC at least including one or more closed leaf pairs and one or more open leaf pairs, the radiation treatment plan including delivery of one or more treatment fractions, the moving including:
    for each closed leaf pair of the one or more closed leaf pairs, determining an offset for each closed leaf pair based on a random value, to obtain one or more offsets corresponding to the one or more closed leaf pairs; and
    causing the one or more closed leaf pairs to move based on the one or more offsets corresponding to the one or more closed leaf pairs, before or during the delivery of one or more treatment fractions.

2. The method of claim 1, wherein the determining an offset for each closed leaf pair comprises:
    designating the random value as the offset.

3. The method of claim 1, further comprising:
    generating the random value for each closed leaf pair by a random number generator.

4. The method of claim 1, wherein the method further comprises:
    generating the offset for each closed leaf pair before or at a beginning of at least one treatment fraction of the one or more treatment fractions.

5. The method of claim 1, wherein at least one treatment fraction of the one or more treatment fractions includes a beam delivery, and the method further comprises:
    generating the offset for each closed leaf pair before or at a beginning of the beam delivery in the at least one treatment fraction of the one or more treatment fractions.

6. The method of claim 1, further comprising:
    determining the offset for each closed leaf pair in a treatment planning process that generates the radiation treatment plan.

7. The method of claim 6, further comprising:
    after determining the offset in the treatment planning process, evaluating or adjusting one or more parameters of the radiation treatment plan based on a leakage distribution associated with a dose leakage of each closed leaf pair.

8. The method of claim 1, wherein the offset of each closed leaf pair is no larger than a predetermined threshold, and the predetermined threshold is determined in a treatment planning process that generates the radiation treatment plan.

9. The method of claim 1, wherein the causing the one or more closed leaf pairs to move comprises:
    causing at least one closed leaf pair of the one or more closed leaf pairs to move, based on at least one offset corresponding to the at least one closed leaf pair, dynamically within at least one treatment fraction of the one or more treatment fractions.

10. The method of claim 1, wherein at least one treatment fraction of the one or more treatment fractions include a beam delivery, and the causing the one or more closed leaf pairs to move comprises:
    causing at least one closed leaf pair of the one or more closed leaf pairs to move, based on at least one offset corresponding to the at least one closed leaf pair, dynamically during the beam delivery in the at least one treatment fraction of the one or more treatment fractions.

11. The method of claim 1, wherein the one or more offsets at least include a first offset and a second offset, and the causing the one or more closed leaf pairs to move comprises:
    causing a first closed leaf pair of the one or more closed leaf pairs to move by the first offset in a first treatment fraction of the one or more treatment fractions; and
    causing the first closed leaf pair of the one or more closed leaf pairs to move by the second offset in a second treatment fraction of the one or more treatment fractions.

12. The method of claim 11, wherein the one or more offsets further include a third offset and a fourth offset, and the causing the one or more closed leaf pairs to move further comprises:
 causing a third closed leaf pair of the at least one closed leaf pair to move by the third offset in a third treatment fraction of the one or more treatment fractions; and
 causing a fourth closed leaf pair of the at least one closed leaf pair to move by the fourth offset in the third treatment fraction of the one or more treatment fractions.

13. The method of claim 1, further comprising causing the one or more open leaf pairs to move according to the radiation treatment plan, wherein the causing the one or more closed leaf pairs to move comprises:
 causing the one or more closed leaf pairs to move based on the one or more offsets corresponding to the one or more closed leaf pairs, synchronously or asynchronously with the moving of the one or more open leaf pairs.

14. The method of claim 1, further comprising:
 determining at least one closed leaf pair from the one or more closed leaf pairs that are uncovered by a jaw.

15. The method of claim 1, further comprising:
 determining, from the one or more closed leaf pairs, a first leaf pair whose state is changed from open to closed; and
 after the first leaf pair is closed, causing the first leaf pair to move by a first offset of the one or more offsets.

16. The method of claim 1, further comprising:
 determining, from the one or more closed leaf pairs, a first leaf pair whose status is changed from closed to open;
 during a period in which the first leaf pair is closed, causing the first leaf pair to move by a first offset of the one or more offsets;
 prior to opening the first leaf pair, causing the first leaf pair to move to a prescribed position according to the radiation treatment plan; and
 causing the first leaf pair to move from the prescribed position according to the radiation treatment plan.

17. The method of claim 1, wherein each closed leaf pair of the one or more closed leaf pairs includes a gap between each closed leaf pair, and the causing the one or more closed leaf pairs to move comprises:
 causing the one or more closed leaf pairs to move based on the one or more offsets corresponding to the one or more closed leaf pairs, so that a position of the gap between each closed leaf pair is adjusted by the offset corresponding to each closed leaf pair.

18. The method of claim 1, wherein the MLC includes at least two layers of leaves, the at least two layers of leaves including a first layer and a second layer, the one or more closed leaf pairs including a first closed leaf pair and a second closed leaf pair, the first layer including the first closed leaf pair, the second layer including the second closed leaf pair, the method further comprising:
 generating a first random value and a second random value independently;
 causing the first closed leaf pair in the first layer to move based on the first random value; and
 causing the second closed leaf pair in the second layer to move based on the second random value.

19. A radiation treatment system for adjusting a multi-leaf collimator (MLC) comprising:
 a drive mechanism configured to drive one or more closed leaf pairs of the MLC to move according to a radiation treatment plan or a portion thereof, the MLC at least including the one or more closed leaf pairs and one or more open leaf pairs, the radiation treatment-plan including delivery of one or more treatment fractions; and
 a controller configured to:
  for each closed leaf pair of the one or more closed leaf pairs, determining an offset for each closed leaf pair based on a random value, to obtain one or more offsets corresponding to the one or more closed leaf pairs; and
  causing the one or more closed leaf pairs to move based on the one or more offsets corresponding to the one or more closed leaf pairs, before or during the delivery of one or more treatment fractions.

20. A radiation treatment system for adjusting a multi-leaf collimator (MLC), comprising:
 at least one storage device storing a set of instructions; and
 at least one processor in communication with the at least one storage device, wherein when executing the set of instructions, the at least one processor is configured to cause the system to perform operations including:
  moving, according to a radiation treatment plan or a portion thereof, one or more leaves of the MLC, the MLC at least including one or more closed leaf pairs and one or more open leaf pairs, the radiation treatment plan including delivery of one or more treatment fractions, the moving including:
  for each closed leaf pair of the one or more closed leaf pairs, determining an offset for each closed leaf pair based on a random value, to obtain one or more offsets corresponding to the one or more closed leaf pairs; and
  causing the one or more closed leaf pairs to move based on the one or more offsets corresponding to the one or more closed leaf pairs, before or during the delivery of one or more treatment fractions.

\* \* \* \* \*